(12) United States Patent
Thompson et al.

(10) Patent No.: US 7,723,475 B2
(45) Date of Patent: May 25, 2010

(54) RTVP-GLIPR-LIKE COMPOSITIONS AND METHODS FOR THE DETECTION, TREATMENT AND PREVENTION OF PROSTATE CANCER

(75) Inventors: Timothy C. Thompson, Houston, TX (US); Chenghui Ren, Houston, TX (US); Chengzhen Ren, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 960 days.

(21) Appl. No.: 11/217,067

(22) Filed: Aug. 31, 2005

(65) Prior Publication Data

US 2006/0210577 A1    Sep. 21, 2006

Related U.S. Application Data

(60) Provisional application No. 60/605,815, filed on Aug. 31, 2004.

(51) Int. Cl.
*C07K 14/00* (2006.01)
*A61K 38/00* (2006.01)

(52) U.S. Cl. .......................................... 530/350; 514/2
(58) Field of Classification Search ........................ None
See application file for complete search history.

(56) References Cited

U.S. PATENT DOCUMENTS 5,856,130 A * 1/1999 Bandman et al. ............ 435/69.1
5,912,143 A * 6/1999 Bandman et al. ........... 435/69.1

OTHER PUBLICATIONS

Murphy et al (Gene 1995;159:131-135.*
Bonaldo et al (Genome Res. 1996; 6(9):791-806).*
Strausburg et al (Proc. Acad. Natl. Sci. 2002; 99(26):16899-16903).*
DeGruijl et al (Nature Medicine 1999; 5410:1124-1125.*
Boon et al (Adv. Can Res 1992;58:177-210).*
Spitler et al (Cacner Biotherapy 1995;10:1-3).*
Ezzell (J. Nih Res. 1995;7:46-49).*
Rich, et al., "RTVP-1, a novel human gene with sequence similarity to genes of diverse species, is expressed in tumor cell lines of glial but not neuronal origin," *Gene* 180:125-130 (1996).

* cited by examiner

*Primary Examiner*—Christopher H Yaen
(74) *Attorney, Agent, or Firm*—Vinson & Elkins L.L.P.

(57) ABSTRACT

The invention is directed to purified and isolated novel RGL2 polypeptides, the nucleic acids encoding such polypeptides, processes for production of recombinant forms of such polypeptides, antibodies generated against these polypeptides, fragmented peptides derived from these polypeptides, and the uses of the above.

11 Claims, 15 Drawing Sheets

FIG. 1A

RGL2α DNA sequence

SEQ ID NO:1     1745 bp

```
   1 GGTGAACCAT GGAGGCCGCA AGGCCCTTCG CCCGGGAGTG GAGGGCCCAG
  51 TCCCTACCCC TGGCAGTAGG GGGCGTTTTG AAGCTGCGGC TCTGTGAGCT
 101 GTGGCTACTG CTACTGGGTT CTAGTTTGAA CGCCAGATTT TTGCCAGACG
 151 AGGAGGACGT AGACTTTATC AACGAGTACG TGAACCTCCA CAATGAGCTG
 201 CGGGGCGACG TCATTCCCCG AGGGTCTAAC TTGCGCTTCA TGACTTGGGA
 251 TGTAGCTTTA TCACGGACTG CTAGAGCATG GGAAAAAAA TGTTTGTTTA
 301 CGCATAATAT TTATTTACAA GATGTACAAA TGGTCCATCC TAAATTTTAT
 351 GGTATTGGTG AAAATATGTG GGTCGGCCCT GAAAATGAAT TTACTGCAAG
 401 TATTGCTATC AGAAGTTGGC ATGCAGAGAA GAAAATGTAC AATTTTGAAA
 451 ATGGCAGTTG CTCTGGAGAC TGTTCTAATT ATATTCAGCT TGTTTGGGAC
 501 CACTCTTACA AAGTTGGTTG TGCTGTTACT CCATGTTCAA AAATTGGACA
 551 TATTATACAT GCAGCAATTT TCATATGCAA CTATGCGCCA GGAGGAACAC
 601 TGACGAGAAG ACCTTATGAA CCAGGAATAT TTTGTACTCG ATGTGGCAGA
 651 CGTGACAAAT GCACAGATTT TCTATGCAGT AAGATAAAGA AAATAAACAT
 701 GAAAAAAATG CATAATGGAT TGGACAAGAA AAATAAGCGA TTAACACTA
 751 GTTTTTTATG GTCATGTTAA TATTATTCCT TTGATCAGAA TGCTACTATT
 801 ATGTTATCAA AGGATGGTTG ACACAGTATC ATCTTTAGAT TTTTCTAAAC
 851 TGCAGAGCTT TTTCTGTTCT ATCTTAACCC TATTCCTTCC CCTGAGGACA
 901 TACCAGAGTG TCAGAAAGAA AGAATGAGAA CTAACAGTTA TACCCTTAAA
 951 AAGCTTCACA GTTTATGCCC AAACAGCAGC CTGTTTGATA ATAACTGCTT
1001 TAAAGGATAG TATATTCCAA AATATTTATG AAGTAGCATA TATTTAATAC
1051 CCTTTTCTTT TAGTTTTTCC TCCAAAAAGC TGAAATCTCC AAATATTTCA
1101 AAAGTAAAAA GTAGAAAATA TGTTTGATTA CATTTTTCTT TTAGTTTTTC
1151 CAAACATGAG AGAATATACT CCAAAAGTAT AACTGTAGCT AAAATATACA
1201 ATGCTTAGAG GAATATGGTA GGAGATAAAT TTGGATAATA AGTAAATAGC
1251 ATATTATGTT GTTTTTTAAT TATTATACTT TAAGTTCTGG GGTACCTGTG
1301 CAGAACGTGC AGGTTTGTTA CATAGGTATA TACATGCCAT GGTGGTTTGC
1351 TGCACCCATG AACCCATCAT CTACATTAGA TATTTCTCCT AAGCTATTCC
1401 TCCCCTAGCC CTGACCCCCT GACAGGCCCC AGTGTGTGAT GTTCTTCTCC
1451 CTGTGTCCAT GTGTTCTCAT TGTTCAACTC CCACTTATGA GTGAGAACAT
1501 GCAGTGTTTG GTTTTCTGTT CTTGTGATAG TTTGCTGAGA ATGATGGTTT
1551 GCAGCTTCAT CCATGTCCCT GAAAAGGAAA TGAACTCATC CTTTTTTATG
1601 GCTGCATAGT ATTCCATGGT GTATATGTGC CACACTTTCT TTATCCAGTC
1651 TATCATTGAT GGGCGTTTGG GTTGGTTCCA AGTATTTGCT ATTGTGAACA
1701 GTGCTGCAAT AAACATATGT TTGCAGGTGA AAAAAAAAA AAAAA
```

FIG. 1B

RGL2β DNA sequence

SEQ ID NO:3     1390 bp

```
   1 ATCTCGGGTA GTTGGGGCCA CTGCTCTGAG GCTGAAGGAT CGCGGAGAAC
  51 CGCACTTTTA GCTTGGTTTT TAAAGTACAC GTGAAGTTTA CACAGAGAAA
 101 AACTGCGGAC ACTCTAACAC ATGCTTATTA CCATGATATT ACACAGGGCC
 151 AGGACTAAGA CTTGGGATGT AGCTTTATCA CGGACTGCTA GAGCATGGGG
 201 AAAAAAATGT TGTTTACGC ATAATATTTA TTTACAAGAT GTACAAATGG
 251 TCCATCCTAA ATTTTATGGT ATTGGTGAAA ATATGTGGGT CGGCCCTGAA
 301 AATGAATTTA CTGCAAGTAT TGCTATCAGA AGTTGGCATG CAGAGAAGAA
 351 AATGTACAAT TTTGAAAATG GCAGTTGCTC TGGAGACTGT TCTAATTATA
```

FIG. 1B (con't)

```
 401  TTCAGCTTGT TTGGGACCAC TCTTACAAAG TTGGTTGTGC TGTTACTCCA
 451  TGTTCAAAAA TTGGACATAT TATACATGCA GCAATTTTCA TATGCAACTA
 501  TGCGCCAGGA GGAACACTGA CGAGAAGACC TTATGAACCA GGAATATTTT
 551  GTACTCGATG TGGCAGACGT GACAAATGCA CAGATTTTCT ATGCAGTAAT
 601  GCAGATCGTG ACCAAGCCAC ATATTACCGA TTTTGGTATC CAAAATGGGA
 651  AATGCCCCGG CCAGTTGTGT GTGATCCACT GTGCACATTC ATTTTATTAT
 701  TGAGAATATT ATGTTTTATC CTGTGTGTCA TAACTGTTTT GATAGTACAG
 751  TCTCAGTTTC CAAATATCTT GTTGGAACAA CAAATGATAT TTACCCCTGA
 801  GGAATCTGAA GCAGGGAATG AAGAGGAGGA AAAAGAGGAA GAGAAGAAAG
 851  AGAAAGAGGA AATGGAAATG GAAATAATGG AAATGGAGGA GGAAAAAGAA
 901  GAGAGAGAGG AGGAGGAGGA GGAAACACAA AAAGAAAAGA TGGAGGAAGA
 951  GGAAAAATAA GAGTAGAAAA AGGAGGAAAA AGATGTATCA CCAATATAAA
1001  CCAAAAGTGT AATACAAAAA AAGACAGAAA AAAAAAAAAA GTAAAACACT
1051  GAGTTTTAAC AAGAAAGAAA ATATGCAAAC CACCATTGGA ATGTTTTTTA
1101  TTCCCTTCTC TCCTATACTT ATTCAATCAA TTTAAATTTG TAAAACAAAG
1151  AAACAAAAAA CATGTAAGGT GGGCTCTTTG ACACTAAGAA CAGATAAAGA
1201  CATGACAGGA AAAACACTGA AAAACATTTG ACCAGTCTAA TTAATCTTAA
1251  GATTTCACCA TGTTATTCTA ATAAAGTAGG GAATTTTCAT TTTCTAAACA
1301  TGTTTCCATC TCTGTGTTTT AAATAGTAAG GTGCTTAAGA TCATTCCAAG
1351  TTCATAACAA CCATTGAATA AAATTTGTAT TTTTTTGTTT
```

FIG. 1C

RGL2γ DNA sequence

SEQ ID NO:5         1090 bp

```
   1  CACTGGCCTG TCAGCGGCCG GTGGACCATG GAGGCCGCAA GGCCCTTCGC
  51  CCGGGAGTGG AGGGCCCAGT CCCTACCCCT GGCAGTAGGG GGCGTTTTGA
 101  AGCTGCGGCT CTGTGAGCTG TGGCTACTGC TACTGGGTTC TAGTTTGAAC
 151  GCCAGATTTT TGCCAGACGA GGAGGACGTA GACTTTATCA ACGAACTTGG
 201  GATGTAGCTT TATCACGGAC TGCTAGAGCA TGGGGAAAAA AATGTTTGTT
 251  TACGCATAAT ATTTATTTAC AAGATGTACA AATGGTCCAT CCTAAATTTT
 301  ATGGTATTGG TGAAAATATG TGGGTCGGCC CTGAAAATGA ATTTACTGCA
 351  AGTATTGCTA TCAGAAGTTG GCATGCAGAG AAGAAAATGT ACAATTTTGA
 401  AAATGGCAGT TGCTCTGGAG ACTGTTCTAA TTATATTCAG CTTGTTTGGG
 451  ACCACTCTTA CAAAGTTGGT TGTGCTGTTA CTCCATGTTC AAAAATTGGA
 501  CATATTATAC ATGCAGCAAT TTTCATATGC AACTATGCGC CAGGAGGAAC
 551  ACTGACGAGA AGACCTTATG AACCAGGAAT ATTTTGTACT CGATGTGGCA
 601  GACGTGACAA ATGCACAGAT TTTCTATGCA GTAATGCAGA TCGTGACCAA
 651  GCCACATATT ACCGATTTTG GTATCCAAAA TGGGAAATGC CCCGGCCAGT
 701  TGTGTGTGAT CCACTGTGCA CATTCATTTT ATTATTGAGA ATATTATGTT
 751  TTATCCTGTG TGTCATAACT GTTTTGATAG TACAGTCTCA GTTTCCAAAT
 801  ATCTTGTTGG AACAACAAAT GATATTTACC CCTGAGGAAT CTGAAGCAGG
 851  GAATGAAGAG GAGGAAAAAG AGGAAGAGAA GAAAGAGAAA GAGGAAATGG
 901  AAATGGAAAT AATGGAAATG GAGGAGGAAA AGAAGAGAG AGAGGAGGAG
 951  GAGGAGGAAA CACAAAAAGA AAAGATGGAG GAAGAGGAAA AATAAGAGTA
1001  GAAAGAGGAG GAAAAGATG TATCACCAAT ATAAACCAAA AGTGTAATCC
1051  AAAAAGGCC AAAAAAAAA AAAAAAAAA AAAAAAAA
```

FIG. 1D

RGL2δ DNA sequence

SEQ ID NO:7        1249 bp

```
   1 GGTGAACCAT GGAGGCCGCA AGGCCCTTCG CCCGGGAGTG GAGGGCCCAG
  51 TCCCTACCCC TGGCAGTAGG GGGCGTTTTG AAGCTGCGGC TCTGTGAGCT
 101 GTGGCTACTG CTACTGGGTT CTAGTTTGAA CGCCAGATTT TTGCCAGACG
 151 AGGAGGACGT AGACTTTATC AACGAGTACG TGAACCTCCA CAATGAGCTG
 201 CGGGGCGACG TCATTCCCCG AGGGTCTAAC TTGCGCTTCA TGACTTGGGA
 251 TGTAGCTTTA TCACGGACTG CTAGAGCATG GGAAAAAAA TGTTTGTTTA
 301 CGCATAATAT TTATTTACAA GATGTACAAA TGGTCCATCC TAAATTTTAT
 351 GGTATTGGTG AAAATATGTG GGTCGGCCCT GAAAATGAAT TTACTGCAAG
 401 TATTGCTATC AGAAGTTGGC ATGCAGAGAA GAAAATGTAC AATTTTGAAA
 451 ATGGCAGTTG CTCTGGAGAC TGTTCTAATT ATATTCAGCT TGTTTGGGAC
 501 CACTCTTACA AAGTTGGTTG TGCTGTTACT CCATGTTCAA AAATTGGACA
 551 TATTATACAT GCAGCAATTT TCATATGCAA CTATGCGCCA GGAGGAACAC
 601 TGACGAGAAG ACCTTATGAA CCAGGAATAT TTTGTACTCG ATGTGGCAGA
 651 CGTGACAAAT GCACAGATTT TCTATGCAGT AATGCAGATC GTGACCAAGC
 701 CACATATTAC CGATTTTGGT ATCCAAAATG GAAATGCCC CGGCCAGTTG
 751 TGTGTGATCC ACTGTGCACA TTCATTTTAT TATTGAGAAT ATTATGTTTT
 801 ATCCTGTGTG TCATAACTGT TTTGATAGTA CAGTCTCAGT TTCCAAATAT
 851 CTTGTTGGAA CAACAAATGA TATTTACCCC TGAGGAATCT GAAGCAGGGA
 901 ATGAAGAGGA GGAAAAAGAG GAAGAGAAGA AAGAGAAAGA GGAAATGGAA
 951 ATGGAAATAA TGGAAATGGA GGAGGAAAAA GAAGAGAGAG AGGAGGAGGA
1001 GGAGGAAACA CAAAAAGAAA AGATGGAGGA GAGGAAAAA TAAGAGTAGA
1051 AAGAGGAGGA AAAAGATGTA TCACCAATAT AAACCAAAAG TGTAATACAA
1101 AAAAAGACAG AAAAAGAAAG TAAAACACTG AGTTTTAACA AGAAAGAAAA
1151 TATGCAAACC ACCATTGGAA TGTTTTTTAT TCCCTTCTCT CCTATACTTA
1201 TTCAATCAAT TTAAATTTGT AAAACAAAGA AACAAAAAAA ATCGAATTC
```

FIG. 1E

RGL2ε DNA sequence

SEQ ID NO:9        1043 bp

```
   1 CACTGGCCTG TCAGCGGCCG GTGGACCATG GAGGCCGCAA GGCCCTTCGC
  51 CCGGGAGTGG AGGGCCCAGT CCCTACCCCT GGCAGTAGGG GGCGTTTTGA
 101 AGCTGCGGCT CTGTGAGCTG TGGCTACTGC TACTGGGTTC TAGTTTGAAC
 151 GCCAGATTTT TGCCAGACGA GGAGGACGTA GACTTTATCA ACGAGTACGT
 201 GAACCTCCAC AATGAGCTGC GGGGCGACGT CATTCCCCGA GGGTCTAACT
 251 TGCGCTTCAT GACTTGGGAT GTAGCTTTAT CACGGACTGC TAGAGCATGG
 301 GAAAAAAAT GTTTGTTTAC GCATAATATT TATTTACAAG ATGTACAAAT
 351 GGTCCATCCT AAATTTTATG GTATTGGTGA AAATATGTGG GTCGGCCCTG
 401 AAAATGAATT TACTGCAAGT ATTGCTATCA GAAGTTGGCA TGCAGAGAAG
 451 AAAATGTACA ATTTTGAAAA TGGCAGTTGC TCTGGAGACT GTTCTAATTA
 501 TATTCAGAGG AACACTGACG AGAAGACCTT ATGAACCAGG AATATTTGT
 551 ACTCGATGTG CAGACGTGA CAAATGCACA GATTTTCTAT GCAGTAATGC
 601 AGATCGTGAC CAAGCCACAT ATTACCGATT TTGGTATCCA AAATGGGAAA
 651 TGCCCCGGCC AGTTGTGTGT GATCCACTGT GCACATTCAT TTTATTATTG
 701 AGAATATTAT GTTTTATCCT GTGTGTCATA ACTGTTTTGA TAGTACAGTC
 751 TCAGTTTCCA AATATCTTGT TGGAACAACA AATGATATTT ACCCCTGAGG
 801 AATCTGAAGC AGGGAATGAA GAGGAGGAAA AAGAGGAAGA GAAGAAAGAG
 851 AAAGGGAAA TGGAAATGGA ATAATGGAA ATGGAGGAGG AAAAAGAAGA
 901 GAGAGAGGAA GAGGAGGAGG AAACACAAAA AGAAAAGATG GAGGAAGAGG
 951 AAAAATAAGA GTAGAAAGAG GAGGAAAAAG ATGTATCACC AATATAAACC
1001 AAAAGTGTAA TGCAAAAAAA AAAAAAAAAA AAAAAAAAAA AAA
```

FIGURE 2

RGL2α, RGL2β, RGL2γ, RGL2δ and RGL2ε proteins compared

```
RGL2_β_      1 ---------------------------------------------------------------
RGL2_γ_      1 ---------------------------------------------------------------
RGL2_δ_      1 MEAARPFAREWRAQSLPLAVGGVLKLRLCELWLLLLGSSLNARFLPDEEDVDFINEYVNL
RGL2_α_      1 MEAARPFAREWRAQSLPLAVGGVLKLRLCELWLLLLGSSLNARFLPDEEDVDFINEYVNL
RGL2_ε_      1 MEAARPFAREWRAQSLPLAVGGVLKLRLCELWLLLLGSSLNARFLPDEEDVDFINEYVNL
consensus    1 meaarpfarewraqslplavggvlklrlcelwllllgsslnarflpdeedvdfineyvnl RGL2_β_      1 -----MLITMILHRARTKTWDVALSRTARAWGKKCLFTHNIYLQDVQMVHPKFYGIGENM
RGL2_γ_      1 ---------------------------------------------MVHPKFYGIGENM
RGL2_δ_     61 HNELRGDVIPRGSNLRFMTWDVALSRTARAWGKKCLFTHNIYLQDVQMVHPKFYGIGENM
RGL2_α_     61 HNELRGDVIPRGSNLRFMTWDVALSRTARAWGKKCLFTHNIYLQDVQMVHPKFYGIGENM
RGL2_ε_     61 HNELRGDVIPRGSNLRFMTWDVALSRTARAWGKKCLFTHNIYLQDVQMVHPKFYGIGENM
consensus   61 hnelrgdviprgsnlrfmtwdvalsrtarawgkkclfthniylqdvqMVHPKFYGIGENM RGL2_β_     56 WVGPENEFTASIAIRSWHAEKKMYNFENGSCSGDCSNYIQLVWDHSYKVGCAVTPCSKIG
RGL2_γ_     14 WVGPENEFTASIAIRSWHAEKKMYNFENGSCSGDCSNYIQLVWDHSYKVGCAVTPCSKIG
RGL2_δ_    121 WVGPENEFTASIAIRSWHAEKKMYNFENGSCSGDCSNYIQLVWDHSYKVGCAVTPCSKIG
RGL2_α_    121 WVGPENEFTASIAIRSWHAEKKMYNFENGSCSGDCSNYIQLVWDHSYKVGCAVTPCSKIG
RGL2_ε_    121 WVGPENEFTASIAIRSWHAEKKMYNFENGSCSGDCSNYIQRNTDEKTL------------
consensus  121 WVGPENEFTASIAIRSWHAEKKMYNFENGSCSGDCSNYIQlvwDhsykvgcavtpcskig RGL2 β     116 HIIHAAIFICNYAPGGTLTRRPYEPGIFCTRCGRRDKCTDFLCSNADRDQATYYRFWYPK
RGL2_γ_     74 HIIHAAIFICNYAPGGTLTRRPYEPGIFCTRCGRRDKCTDFLCSNADRDQATYYRFWYPK
RGL2 δ     181 HIIHAAIFICNYAPGGTLTRRPYEPGIFCTRCGRRDKCTDFLCSNADRDQATYYRFWYPK
RGL2_α_    181 HIIHAAIFICNYAPGGTLTRRPYEPGIFCTRCGRRDKCTDFLCSKIKKINMKKMHNGLDK
RGL2_ε_        ------------------------------------------------------------
consensus  181 hiihaaificnyapggtltrrpyepgifctrcgrrdkctdflcsnadrdqatyyrfwypk RGL2 β     176 WEMPRPVVCDPLCTFILLLRILCFILCVITVLIVQSQFPNILLEQQMIFTPEESEAGNEE
RGL2_γ_    134 WEMPRPVVCDPLCTFILLLRILCFILCVITVLIVQSQFPNILLEQQMIFTPEESEAGNEE
RGL2 δ     241 WEMPRPVVCDPLCTFILLLRILCFILCVITVLIVQSQFPNILLEQQMIFTPEESEAGNEE
RGL2_α_    241 KNKRLNTSFLWSC-----------------------------------------------
RGL2 ε         ------------------------------------------------------------
consensus  241 wemprpvvcdplctfilllrilcfilcvitvlivqsqfpnilleqqmiftpeeseagnee RGL2_β_    236 EEKEEEKKEKEEMEMEIMEMEEEKEEREEEEEETQKEKMEEEEK    SEQ ID NO. 4
RGL2_γ_    194 EEKEEEKKEKEEMEMEIMEMEEEKEEREEEEEETQKEKMEEEEK    SEQ ID NO. 6
RGL2 δ     301 EEKEEEKKEKEEMEMEIMEMEEEKEEREEEEEETQKEKMEEEEK    SEQ ID NO. 8
RGL2_α_        -------------------------------------------    SEQ ID NO. 2
RGL2_ε_        -------------------------------------------    SEQ ID NO. 10
consensus  301 eekeeekkekeememeimemeeekeereeeeetqkekmeeeek
```

FIGURE 4
Chromosome localization of *RTVP-1/RGL* gene cluster
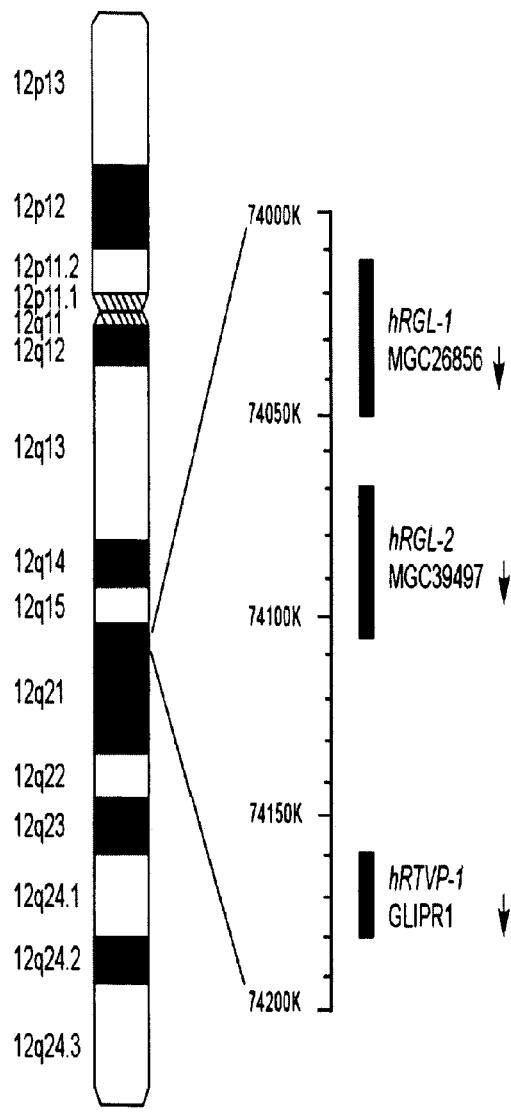
A  Human *RTVP-1* gene cluster
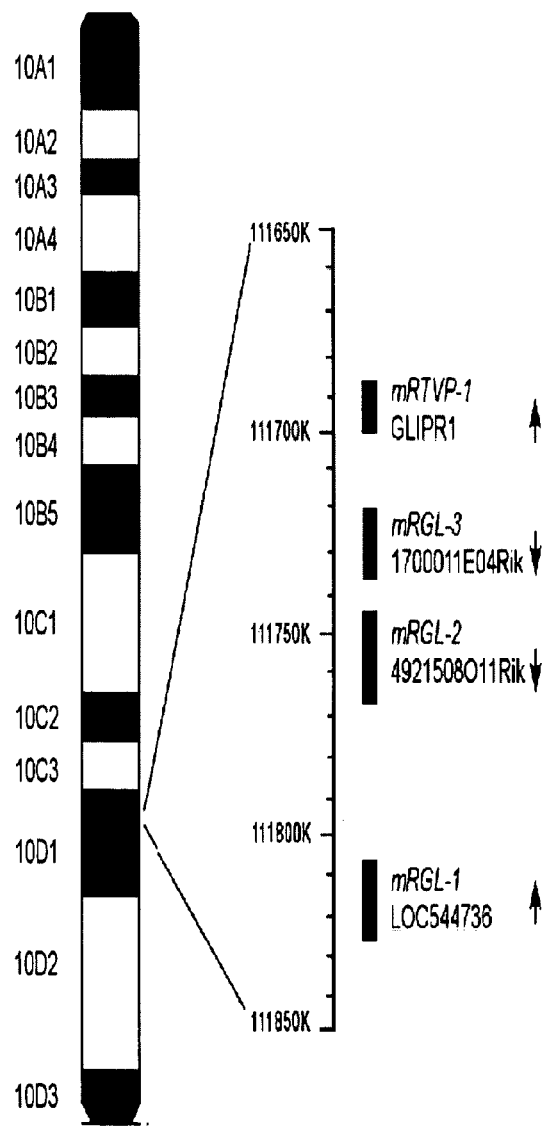
B  Mouse *RTVP-1* gene cluster

FIGURE 5
p53-Induced expression by p53 sites in Human RTVP-1 and RGL2 genes
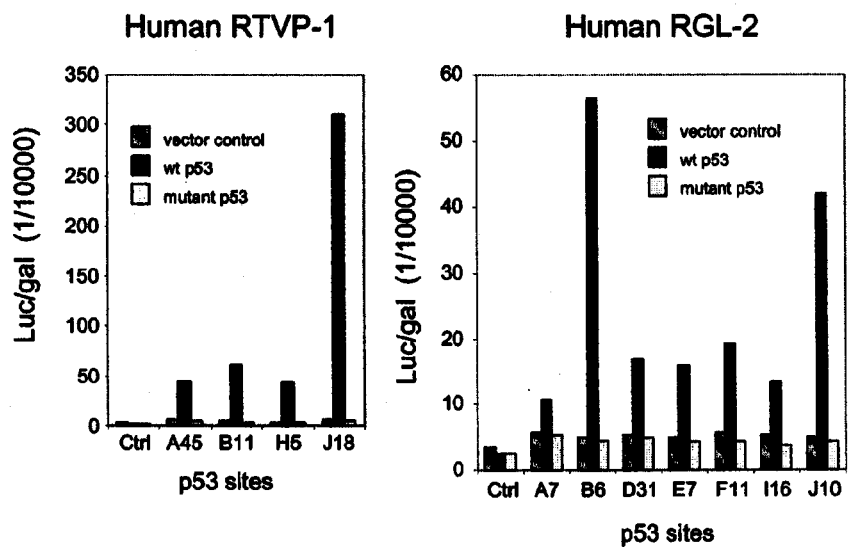
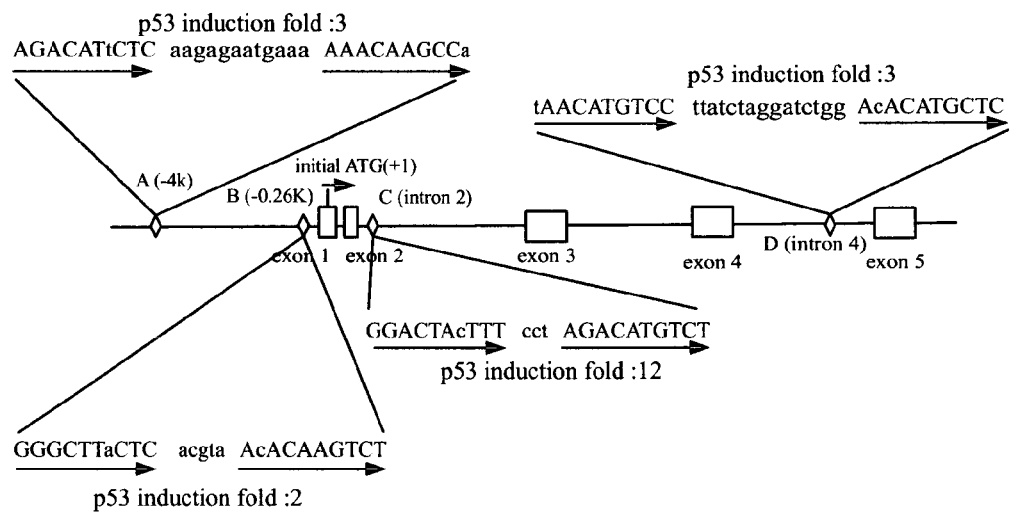
P53 cbs: RRRCWWGYYY (n) RRRCWWGYYY DNA Fragmentation Induced by hRGL2 Expression (4 stable TSU-Pr1 cell lines with doxycycline-induced expression of RGL2α or RGL2β)

FIGURE 9
A) 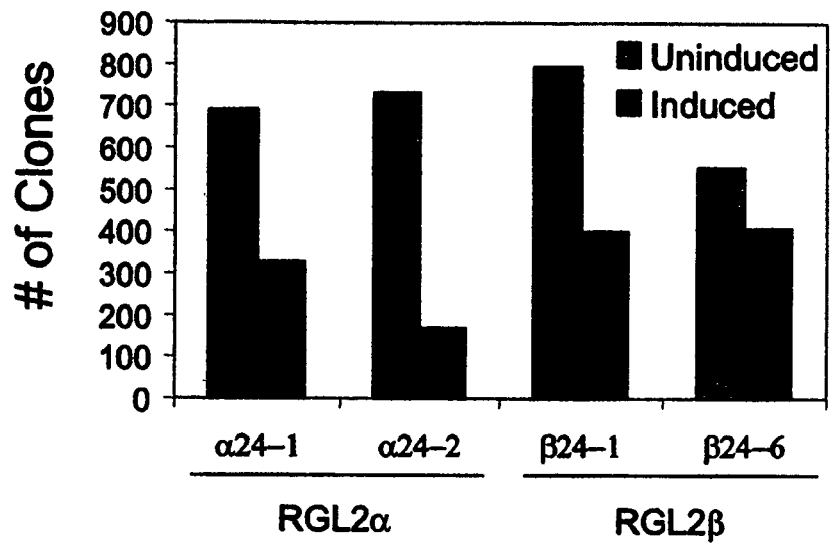
Clone-forming Ability of Cell-lines Expressing hRGL2
(4 stable TSU-Pr1 cell lines with doxycycline-induced expression of RGL2α or RGL2β)
B) 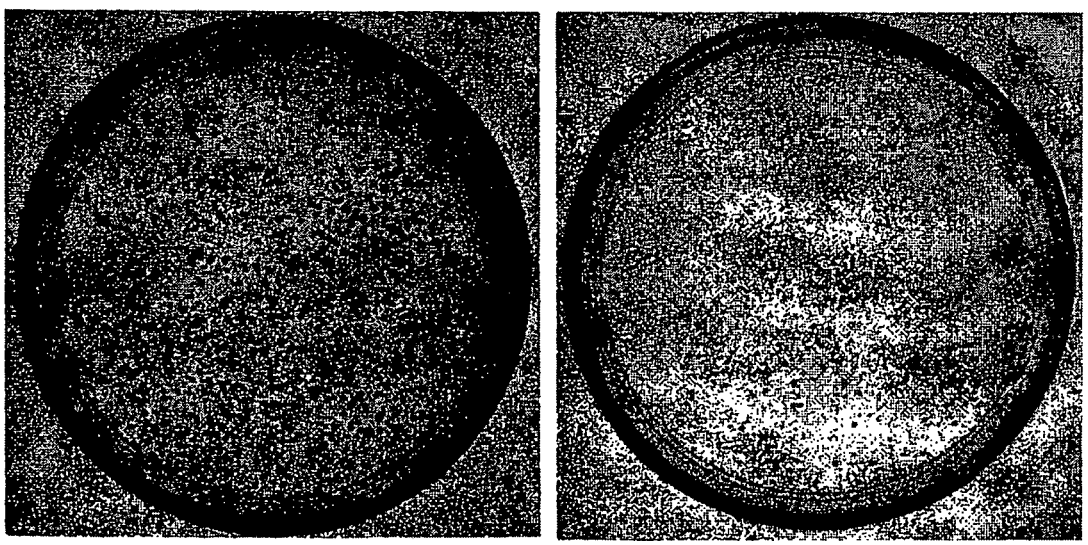
No RGL2α Expression | RGL2α Expression Turned On

FIGURE 10
A)
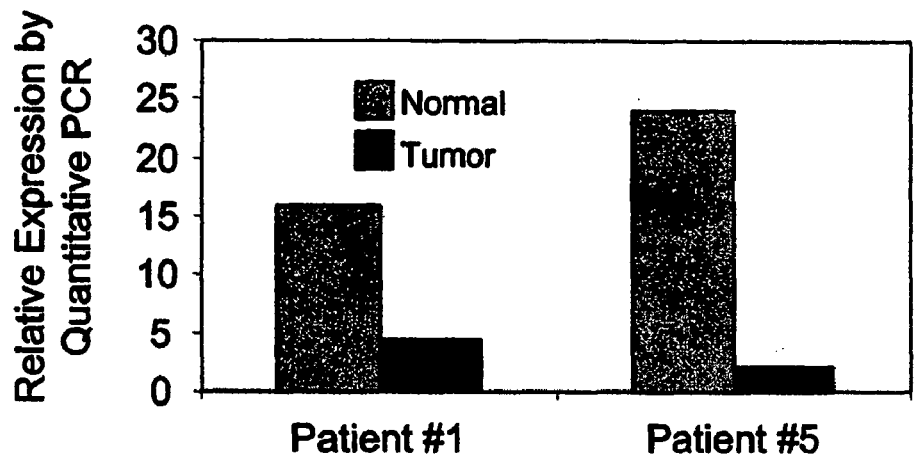
B)
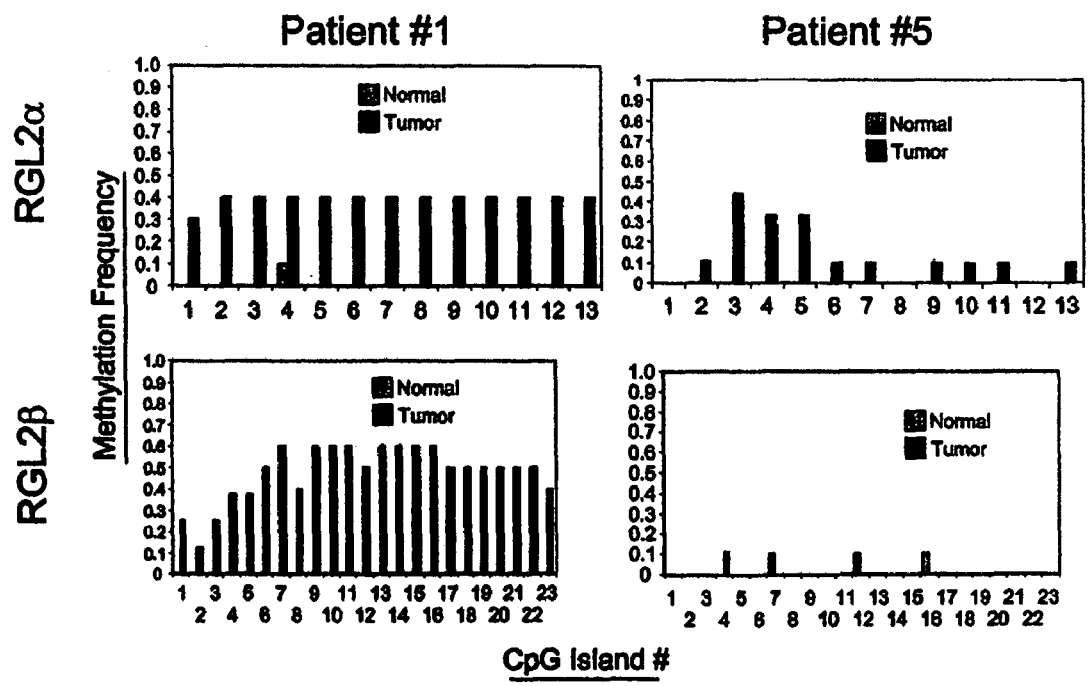

FIGURE 11
β-gal (-neg) 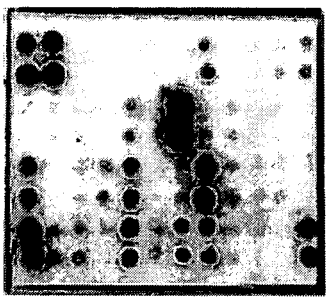
p144 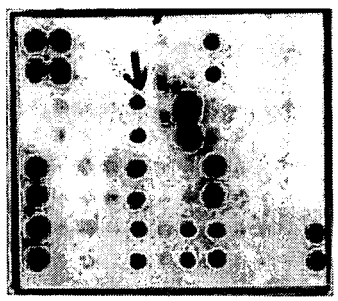
hRTVP 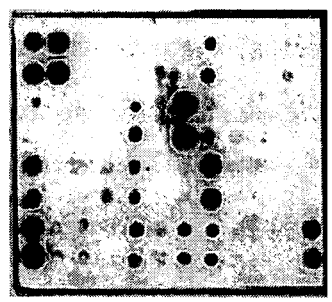
RGL1α 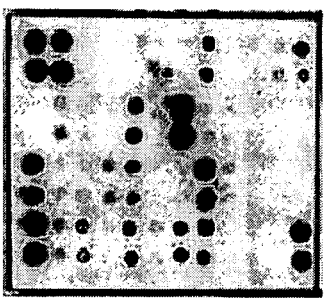
RGL1β 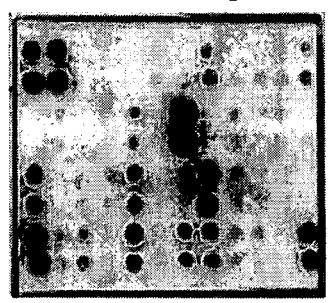
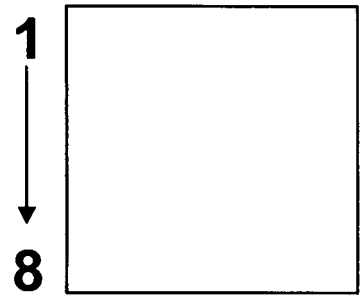
RGL2α 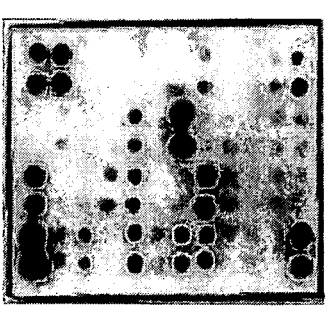
RGL2β 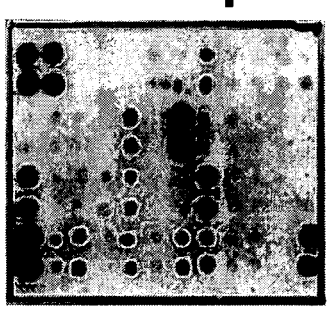
A7-8 = TNFα
E3-4 = IL-6
G3-4 = IL-8
L1-2 = IL-1β
H1-2 = GRO

FIGURE 12
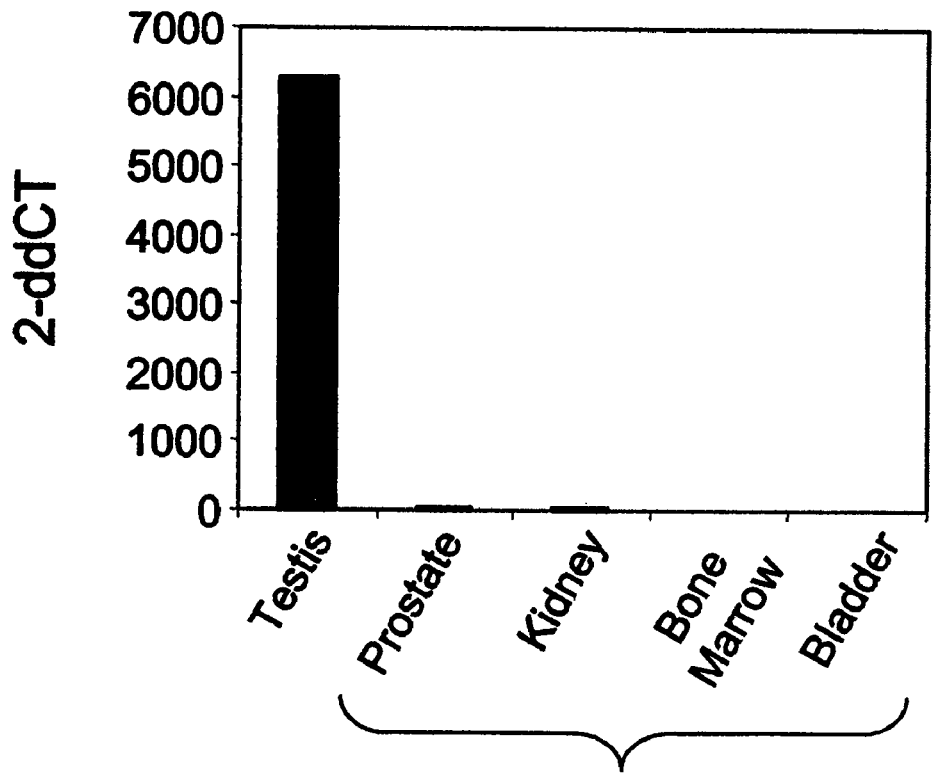
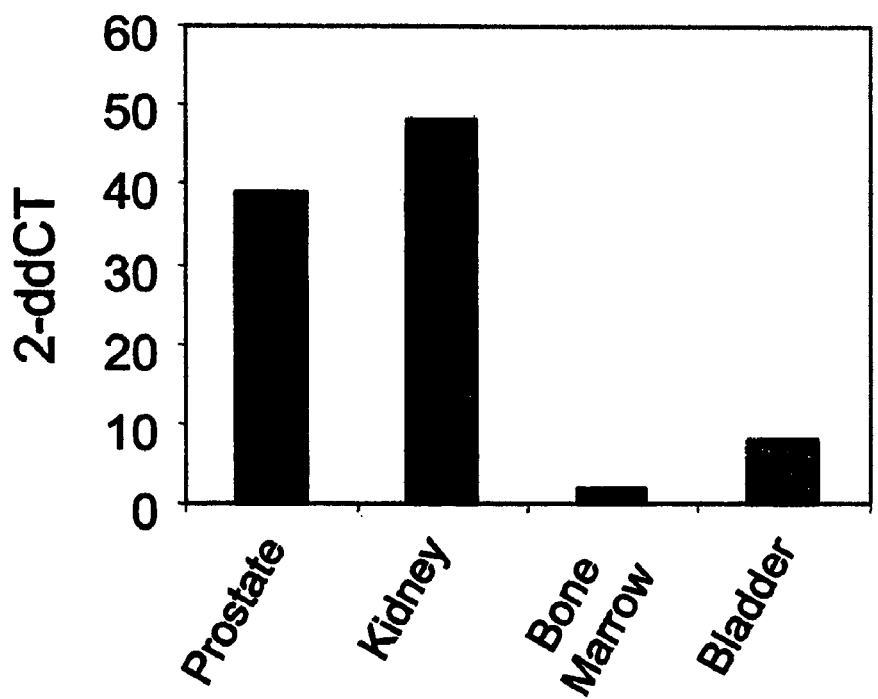

In vivo Tumor-killing by RGL2-family Parent, RTVP-1 in a Xenograft Tumor Model

RTVP-GLIPR-LIKE COMPOSITIONS AND METHODS FOR THE DETECTION, TREATMENT AND PREVENTION OF PROSTATE CANCER

RIGHTS IN THE INVENTION

The invention was made with support from the United States government under grant numbers RO1-CA50588 and P50-CA58204, awarded by the National Institutes of Health, and the United States government has certain rights in this invention.

BACKGROUND OF THE INVENTION

1. Field of the Invention

The present invention is directed to purified and isolated RTVP-1-G1iPR-like polypeptides ("RGL polypeptides") and fragments thereof, the nucleic acids encoding such polypeptides, processes for production of recombinant forms of such polypeptides, antibodies generated against these polypeptides, fragmented peptides derived from these polypeptides, and uses thereof. In particular, the invention relates to compositions and methods for the detection, treatment and prevention of metastatic and other neoplastic disorders.

2. Description of Related Art

Cancer cells may be are defined by two heritable properties, uncontrolled growth and uncontrolled invasion of normal tissue. A cancerous cell can divide in defiance of the normal growth constraints in a cell leading to a localized growth or tumor. In addition, some cancer cells may become metastatic, gaining the ability to migrate away from their initial site and invade other tissues areas and types. It is the combination of these two features that make a cancer cell especially dangerous.

An isolated abnormal cell population that grows uncontrollably will give rise to a tumor or neoplasm. As long as the neoplasm remains non-invasively in a single location, it is said to be benign, and a complete cure may be expected by removing the mass surgically. A tumor or neoplasm is counted as a cancer if it is malignant, that is, if its cells have the ability to invade surrounding tissue. True malignancy begins when the cells cross the basal lamina and begin to invade the underlying connective tissue. Malignancy also occurs when the cells gain the ability to detach from the main tumor mass, enter the bloodstream or lymphatic vessels, and form secondary tumors or metastases at other sites in the body. The more widely a tumor metastasizes, the harder it is to eradicate and treat.

As determined from epidemiological and clinical studies, most cancers develop in slow stages from mildly benign into malignant neoplasms. Malignant cancer usually begins as a benign localized cell population with abnormal growth characteristics called dysplasia. The abnormal cells acquire abnormal growth characteristics resulting in a neoplasia characterized as a cell population of localized growth and swelling. If untreated, the neoplasia in situ may progress into a malignant neoplasia. Several years, or tens of years may elapse from the first sign of dysplasia to the onset of full blown malignant cancer. This characteristic process is observed in a number of cancers. Prostate cancer provides one of the clearest examples of the progression of normal tissue to benign neoplasm to malignant neoplasm.

Prostate cancer is the most common malignancy in men in the USA, resulting in an estimated 41,800 deaths in 1997. (Parker S L, et at, CA Cancer J. Clin. 47: 5-27, 1997). The widespread use of prostate-specific antigen (PSA) has dramatically increased the number of patients diagnosed with prostate cancer and generally lowered the stage of disease at diagnosis. (Scardino P T, Urol. Clin. N. Am. 16:635-655, 1989; Epstein J L, et al., JAMA 271: 368-374, 1994). Nevertheless, 5%-10% of cancers detected by PSA screening are clinically advanced and not candidates for radical prostatectomy. Despite surgical removal of the prostate, 30%-60% of men treated will have recurrence of cancer within 5 years, suggesting that the clinical stage of the patients undergoing surgery was highly inaccurate. 20%-57% of patients undergoing definitive surgery with presumed localized disease will have rising PSA following treatment, also indicative of local or distant residual disease. (Ohori M, et al., J. Urol. 154: 1818-1824, 1995; Zeitman A L, et al., Urology 43: 828-833, 1994). Neither of these conditions is amenable to curative therapy.

The walnut-sized prostate is an encapsulated organ of the mammalian male urogenital system. Located at the base of the bladder, the prostate is partitioned into zones referred to as the central, peripheral and transitional zones, all of which surround the urethra. Histologically, the prostate is a highly microvascularized gland comprising fairly large glandular spaces lined with epithelium which, along with the seminal vesicles, supply the majority of fluid to the male ejaculate. As an endocrine-dependent organ, the prostate responds to both the major male hormone, testosterone, and the major female hormones, estrogen and progesterone. Testicular androgen is considered important for prostate growth and development because, in both humans and other animals, castration leads to prostate atrophy and, in most cases, an absence of any incidence of prostatic carcinoma.

The major neoplastic disorders of the prostate are benign enlargement of the prostate, also called benign prostatic hyperplasia (BPH), and prostatic carcinoma, a type of neoplasia. BPH is very common in men over the age of 50. It is characterized by the presence of a number of large distinct nodules in the periurethral area of the prostate. Although benign and not malignant, these nodules can produce obstruction of the urethra causing nocturia, hesitancy to void, and difficulty in starting and stopping a urine stream upon voiding the bladder.

In its more aggressive form, malignant transformed prostatic tissues escape from the prostate capsule and metastasize invading locally and throughout the bloodstream and lymphatic system. Metastasis, defined as tumor implants which are discontinuous with the primary tumor, can occur through direct seeding, lymphatic spread and hematogenous spread. All three routes have been found to occur with prostatic carcinoma. Local invasion typically involves the seminal vesicles, the base of the urinary bladder, and the urethra. Direct seeding occurs when a malignant neoplasm penetrates a natural open field such as the peritoneal, pleural or pericardial cavities. Cells seed along the surfaces of various organs and tissues within the cavity or can simply fill the cavity spaces. Hematogenous spread is typical of sarcomas and carcinomas. Hematogenous spread of prostatic carcinoma occurs primarily to the bones, but can include massive visceral invasion as well. It has been estimated that about 60% of newly diagnosed prostate cancer patients will have metastases at the time of initial diagnosis.

Surgery or radiotherapy is the treatment of choice for early prostatic neoplasia. Surgery involves complete removal of the entire prostate (radical prostatectomy), and often removal of the surrounding lymph nodes, or lymphadenectomy. Radiotherapy, occasionally used as adjuvant therapy, may be either external or interstitial using 125I. Endocrine therapy is the treatment of choice for more advanced forms. The aim of this therapy is to deprive the prostate cells, and presumably the transformed prostate cells as well, of testosterone. This is accomplished by orchiectomy (castration) or administration of estrogens or synthetic hormones which are agonists of luteinizing hormone-releasing hormone. These cellular messengers directly inhibit testicular and organ synthesis and suppress luteinizing hormone secretion which in turn leads to reduced testosterone secretion by the testes. In normal prostate, removal of androgenic hormones results in regression of the gland involving apoptosis of more than 60% of the luminal epithelial cells. Although often initially sensitive to removal of androgens, prostate cancer cells eventually lose this response and continue to grow and spread even in the absence of androgenic steroids. Despite the advances made in achieving a pharmacologic orchiectomy, the survival rates for those with late stage carcinomas are rather bleak.

Current therapeutic regimens for metastatic disease typically involve both chemical and surgical androgen ablation, which although has been demonstrated to extend life when compared to untreated patients, almost invariably results in the development of hormone-refractory disease and the demise of the patient. The fundamental concepts upon which current androgen ablation therapy was developed were reported more than 50 years ago by Huggins and Hodges. (Huggins C, et al., Cancer Res. 1:293-297, 1941). These experiments reported the phenomenon in which removal of androgenic steroids by castration resulted in reduced growth and biochemical activities in prostate cancer.

With the advent of molecular biology, various investigators in laboratories have attempted to understand the molecular biology of castration-induced regression of the prostate at a more mechanistic level. The model systems selected almost invariably compared mRNAs produced prior to castration and during castration-induced regression using rat prostate model systems in vivo. These model systems yield gene activities that may be involved in castration-induced regression but could also be involved in activities that are not directly relevant or related to castration-induced regression but were stimulated by removal of androgenic steroids. It is anticipated that only a small fraction of gene activities modulated by steroid withdrawal would indeed be involved in castration-induced regression and, therefore, significant confounding background activity would be seen in these existing model systems. There is therefore a need for a model system in which the androgenic-stimulated gene activities not associated with castration-induced regression, or "background" gene activities, would be normalized. Moreover, a better understanding of the molecular basis of metastasis, in prostate cancer, as well as other forms of cancer, would allow rational efforts toward the development of novel effective anti-metastatic therapy to proceed.

One such advancement in the understanding of the molecular basis of prostate cancer has occurred through the study of p53. It has been shown that there exists a specific and established association between loss of p53 function and prostate cancer metastasis. Recent studies demonstrated that specific p53 mutations are clonally expanded in metastatic prostate cancer (Stapleton, A M. et al., Clin Cancer Res 3, 1389-97, 1997) and that a pattern of aberrant p53 expression in primary tumors, termed "clustered p53 staining," has significant prognostic value in predicting recurrence following radical prostatectomy (Quinn, D. I. et. al., Cancer Res 60, 1585-94, 2000 and Stapleton, A M. et. al., Cancer 82, 168-75, 1998). It is generally considered that the nature of functional alterations which occur in cells containing p53 mutations specifically facilitates metastatic seeding, survival, and growth at distant metastatic sites. These alterations likely result, in part, from aberrant regulation of genes under the transcriptional control of p53 that have previously been shown to mediate apoptosis (el-Deiry, W. S., Setnin Cancer Biol 8, 345-57, 1998; Miyashita, T. & Reed, S. C., Cell 80, 293-9, 1995; Sheikh, M S. et. al., Cancer Res 58, 1593-8, 1998; Oda, K. et. al., Cell 102, 849-62, 2000; and Zhu, J. & Chen, Mol Cell Biol 20, 5602-18, 2000) and anti-angiogenic activities (Dameron, K. M., Volpert, O. V., Tainsky, M. A. & Bouck, N., Science 265, 1582-4, 1994; Lopez-Ocejo, 0. et. al., Oncogene 19, 4611-20, 2000; Zou, Z. et. al., J Biol Chem 275, 6051-4, 2000; Zhang, M., Volpert, O., Shi, Y. H. & Bouck, N., Nat Med 6, 196-9, 2000; and Zhang, Y., Griffith, E. C., Sage, S., Jacks, T. & Liu, J. O., Proc Natl Acad Sci USA 97, 6427-32, 2000).

Surprisingly, it has been discovered that certain proteins related to testes-specific, vespid and pathogenic proteins ("RTVP-related" or "RTVP-like" proteins), are up-regulated by p53 in mouse prostate cancer cells. Proteins which are Related to Testes-specific, Vespid and Pathogenic proteins include those proteins with homology to mammalian testes-specific proteins (e.g. TPXI), plant pathogenesis-related proteins (e.g. PR-protein such as subtype 1, PR-lb), vespid venom allergan proteins (antigen 5), or combinations thereof. Homology means that there is a relevant degree of similarity in the amino acid sequence between a polypeptide of the invention and one or more of the proteins mammalian testes-specific proteins, plant pathogenesis proteins and vespid venom allergan antigen 5, or in the respective gene sequences. Relevant homology means that the degree of amino acid sequence similarity is about 35% or greater, preferably about 45% or greater, more preferably about 60% or greater, and even more preferably about 75% or greater. Homology can be determined directly by sequencing the polypeptide of interest and comparing it with the known sequence, or experimentally by methods well know to those or ordinary skill in the art. Homology can be determined using, for example, blastp queries at default settings for amino acid homology determinations, and using blastn queries at default settings for nucleic acid homology determinations.

SUMMARY OF THE INVENTION

The invention aids in fulfilling these various needs in the art by providing isolated RTVP-related nucleic acids and polypeptides encoded by these nucleic acids. Particular embodiments of the invention are directed to an isolated "RGL2" nucleic acid molecule ("RGL2-alpha") comprising the DNA sequence of SEQ ID NO: 1 or four isolated alternate forms ("RGL2-beta", "RGL2-gamma", "RGL2-delta" and "RGL2-epsilon") comprising the DNA sequences of SEQ ID NO: 3, SEQ ID NO: 5, SEQ ID NO: 7 and SEQ ID NO: 9, respectively, as well as isolated RGL2 nucleic acid molecules encoding the amino acid sequence of SEQ ID NO: 2, SEQ ID NO: 4, SEQ ID NO: 6, SEQ ID NO: 8 and SEQ ID NO: 10, and nucleic acid molecules complementary to these sequences. Both single-stranded and double-stranded RNA and DNA nucleic acid molecules are encompassed by the invention, as well as nucleic acid molecules that hybridize to a denatured, double-stranded DNA comprising all or a portion of SEQ ID NO: 1, 3, 5, 7 or 9. Also encompassed are isolated nucleic acid molecules that are derived by in vitro mutagenesis of nucleic acid molecules comprising sequences of SEQ ID NO: 1, 3, 5, 7 or 9, that are degenerate from nucleic acid molecules comprising sequences of SEQ ID NO: 1, 3, 5, 7 or 9, and that are allelic variants of DNA of the invention. The invention also encompasses recombinant vectors that direct the expression of these nucleic acid molecules and host cells stably or transiently transformed or transfected with these vectors.

In addition, the invention encompasses methods of using the nucleic acids noted above to identify nucleic acids encoding proteins having anti-neoplastic activity, especially with regard to genitourinary tumors, such as prostate and testicular cancers, or other human conditions associated with p53 or RTVP-1 activity.

The invention also encompasses the use of sense, antisense oligonucleotides or siRNA from the nucleic acid of SEQ ID NO: 1, 3, 5, 7 or 9 to either increase or inhibit the expression of the polynucleotide encoded by the RGL2 gene.

The invention also encompasses isolated polypeptides and fragments thereof encoded by these nucleic acid molecules, including soluble or secreted polypeptide portions of SEQ ID NO: 2, 4, 6, 8 or 10. The invention further encompasses methods for the production of these polypeptides, including culturing a host cell under conditions promoting expression and recovering the polypeptide from the culture medium Especially, the expression of these polypeptides in bacteria, yeast, plant, insect, and animal cells is encompassed by the invention.

In general, the polypeptides of the invention can be used to advance the diagnosis and treatment of conditions associated with the cellular processes of apoptosis and neoplasia. For example, the invention includes assays utilizing these polypeptides to screen for potential inhibitors of neoplastic activity associated with polypeptide counter-structure molecules, as well as methods of using these polypeptides as to study cellular processes associated with oncogenic diseases which may be modulated by RTVP-related polypeptide molecules. Further, methods of using these polypeptides in the design of inhibitors thereof are also an aspect of the invention.

Further encompassed by this invention are methods and compositions to aid in the detection and treatment of neoplastic disorders, especially genitourinary tumors, such as prostate and testicular cancers, including the use of the RGL2 promoter to drive the targeted expression of anti-neoplastic molecules.

Isolated polyclonal or monoclonal antibodies that bind to these RGL2 polypeptides are also encompassed by the invention, in addition the use of these antibodies to aid in purifying the polypeptides, as well as in the detection and treatment of neoplastic disorders.

BRIEF DESCRIPTION OF THE FIGURES

FIG. 1A presents the nucleotide sequences of RGL1-alpha (SEQ ID NO:1), FIG. 1B presents the nucleotide sequence of RGL2-beta (SEQ ID NO:3), FIG. 1C presents the nucleotide sequence of RGL2-gamma SEQ ID NO:5), FIG. 1D presents the nucleotide sequence of RGL2-delta (SEQ ID NO:7), and FIG. 1E presents the nucleotide sequence of RGL2-epsilon (SEQ II) NO:9).

FIG. 2 presents the amino acid sequences of RGL2-alpha (SEQ ID NO:2), RGL2-beta (SEQ ID NO:4), RGL2-gamma (SEQ ID NO:6), RGL2-delta (SEQ ID NO:8) and RGL2-epsilon (SEQ ID NO:10) in comparison to one another. The consensus sequence was derived from an alignment of all 5 isoforms of RGL2. The consensus amino acid sequence is the same as the RGL2-delta isoform, (SEQ ID NO:8).

FIG. 4 shows genomic maps of human chromosome 12 and mouse chromosome 10 with the location of the RTVP-family genes indicated.

FIG. 5 demonstrates how p53 regulates expression of the RGL2 gene. Various p53 binding sites from the RGL2 promoters increase expression of a reporter gene (luciferase) under control of a minimal promoter when wild-type p53 is expressed in the same cell. The left graph is a positive control using p53 sites from the human RTVP-1 gene. The bottom of the figure presents the location and sequence of selected p53 binding sites in the human RGL2 gene locus.

FIG. 9 demonstrates that the efficiency of colony formation by TSUPr1 cells is reduced when the expression of RGL2-alpha or RGL2-beta is induced. The bottom of the figure photographically shows these same results for the 24-1 clone expressing RGL2-alpha.

FIG. 10 part (A) shows that expression of RGL2 is reduced in the tumor tissue of 2 prostate cancer patients relative to normal tissue from the same patients. FIG. 10 part (B) shows that this reduction in expression is correlated with an increased proportion of CpG islands being methylated in the RGL2 promoters.

FIG. 11 shows the results of testing an array of immune-system related products for either up or down regulation in response to the expression of various RTVP-1 family genes including human RGL2-alpha and RGL2-beta. The mouse RTVP-1 is labeled p144 and (3gal is a negative control. Selected proteins of interest such as IL-6 are identified by providing coordinates corresponding to that protein's antibody's position on the array.

FIG. 12 is a graph of results from quantitative-PCR analysis of expression of the RGL2 message in various tissues. Results are expressed in arbitrary but relative units. The bottom graph segregates prostate, kidney, bone marrow and bladder from testes to better resolve their relative expression levels. The highest expression is seen in testes, with significant expression in prostate, kidney and bone marrow.

DETAILED DESCRIPTION OF THE INVENTION

Figure 3:
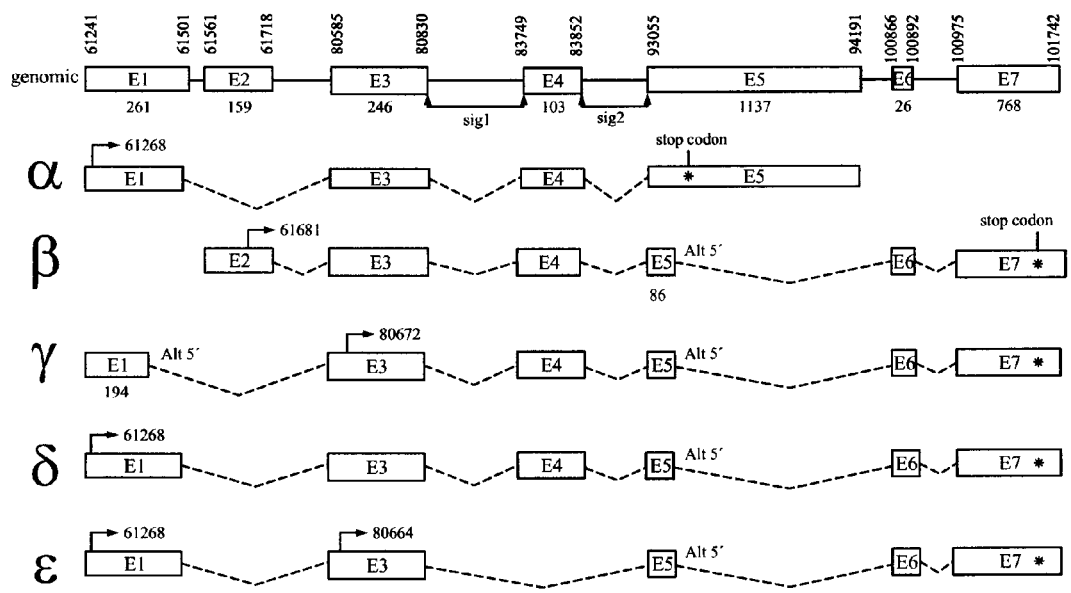
FIG. 3 presents the genomic structure of the human RGL2 locus indicating the relative size and position of its 7 exons and how those exons are spliced to generate the 5 spliced isoforms of the human RGL2 gene.

The present disclosure arises from the discovery of a gene encoding a homologue of RTVP/GLPr genes and the surprising discovery of several splice variants of the RGL2 gene, as well as the novel finding that at least the RGL2-alpha and RGL2-beta isoforms are capable of inducing apoptosis in and suppressing the cell growth of a cancerous prostate cell line.

The nucleic acid molecules encompassed in the invention include the following nucleotide sequences (shown in FIG. 1A-E).

SEQ ID NO.: 1 representing the nucleotide sequence of RGL2-alpha.

SEQ ID NO.: 3 representing the nucleotide sequence of RGL2-beta.

SEQ ID NO.: 5 representing the nucleotide sequence of RGL2-gamma.

SEQ ID NO.: 7 representing the nucleotide sequence of RGL2-delta.

SEQ ID NO.: 9 representing the nucleotide sequence of RGL2-epsilon.

The amino acid sequences of the polypeptides encoded by the nucleotide sequence of the invention includes (shown in FIG. 2):

SEQ ID NO.: 2 representing the amino acid sequence of RGL2-alpha.

SEQ ID NO.: 4 representing the amino acid sequence of RGL2-beta.

SEQ ID NO.: 4 representing the amino acid sequence of RGL2-gamma.

SEQ ID NO.: 4 representing the amino acid sequence of RGL2-delta.

SEQ ID NO.: 4 representing the amino acid sequence of RGL2-epsilon.

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acids encoding proteins having anti-neoplastic activity; the use of the nucleic acids or oligonucleotides thereof to identify human chromosome number 12q on which the RGL2 gene is located; the use of the nucleic acids or oligonucleotides thereof to map genes on human chromosome number 12q; the use of the nucleic acids or oligonucleotides thereof to identify and treat certain diseases, syndromes or other human conditions associated neoplastic disorders, especially prostate cancer and cancers of the genitourinary tract; the use of single-stranded sense or antisense oligonucleotides from the nucleic acids to inhibit expression of polynucleotide encoded by the RGL2 gene; the use of such polypeptides and soluble or secreted fragments thereof to inhibit neoplastic activity(s); and the use of antibodies to purify RTVP-related polypeptides, especially RGL2 polypeptides or fragments thereof.

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the corresponding complementary sequences. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO: 1, 3, 5, 7 or 9 or a suitable fragment thereof, as a probe.

The DNA molecules of the invention include full length genes as well as polynucleotides and fragments thereof Other embodiments include DNA encoding a soluble or secreted form of a protein, e.g., fragments comprising the extracellular domains of the protein, either with or without a signal peptide.

The nucleic acids of the invention are preferentially derived from human sources, but the invention includes those derived from non-human species, as well.

Preferred Sequences

A particularly preferred nucleotide sequence of the invention is SEQ ID NO:1, 3, 5, 7 or 9, as set forth in FIGS. 1A-E. The sequences of amino acids encoded by the DNA of SEQ ID NOs:1, 3, 5, 7 and 9 are shown as SEQ ID NOs:2, 4, 6, 8 and 10, respectively, in FIG. 2. Based on homology parameters discussed above, the RGL2 polynucleotide is a member of the RTVP family containing p53 binding sites within its promoter, a signal peptide and two SGP-domains (i.e.: "small G protein" domains).

Additional Sequences

Due to the known degeneracy of the genetic code, wherein more than one codon can encode the same amino acid, a DNA sequence can vary from that shown in SEQ ID NO: 1, 3, 7 or 9 and still encode a polypeptide having the amino acid sequence of SEQ ID NOs: 2, 4, 8, or 10, respectively. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO: 1, 3, 5, 7 or 9 (b) DNA encoding the polypeptides of SEQ ID NOs: 2, 4, 6, 8, or 10; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

The basic parameters affecting the choice of hybridization conditions and guidance for devising suitable conditions are set forth by Sambrook et al., 1989. As used herein, conditions of moderate stringency can be readily determined by those having ordinary skill in the art based on, for example, the length and/or base composition of the DNA. For hybridizing probes longer than about 100 nucleotides with filter-bound target DNA or RNA, one way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 42° C. (or other similar hybridization solutions, such as one containing about 50% formamide, with a hybridization temperature of about 42° C.), and washing conditions of about 60° C., in 0.5×SSC, 0.1% SDS. Conditions of high stringency can also be readily determined by the skilled artisan based on, for example, the length and base composition of the DNA. Generally, such conditions are defined as hybridization conditions as above, but with washing at approximately 68° C., 0.2×SSC, 0.1% SDS. It should be understood that the wash temperature and wash salt concentration can be adjusted as necessary to achieve a desired degree of stringency by applying the basic principles that govern hybridization reactions and duplex stability, as known to those skilled in the art (see, e.g., Sambrook et al., 1989). It should be further understood that hybridization conditions for oligonucleotide probes of defined length and sequence can be designed by applying formulae known in the art (e.g., see Sambrook et al., 1989, at 11.45-11.47).

Also included as an embodiment of the invention is DNA encoding polypeptide fragments and polypeptides comprising conservative amino acid substitution(s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et at (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a RGL2 (alpha, beta, gamma, delta or epsilon) polypeptide, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et at, Science 239:487 (1988); *Recombinant DNA Methodology*, Wu et al., eds., Academic Press, Inc., San Diego (1989), pp. 189-196; and *PCR Protocols: A Guide to Methods and Applications*, Innis et at, eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

Polypeptides and Fragments Thereof

The polypeptides of the invention include full length proteins encoded by the nucleic acid sequences set forth above. Particularly preferred polypeptides comprise the amino acid sequence of SEQ ID NO: 2, 4, 6, 8 or 10.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may include the cytoplasmic domain, or a portion thereof, as long as the polypeptide is secreted from the cell in which it is produced.

In general, the use of soluble forms is advantageous for certain applications. Purification of the polypeptides from recombinant host cells is facilitated, since the soluble polypeptides are secreted from the cells. Further, soluble polypeptides are generally more suitable for therapeutic or research based intravenous administration.

The invention also provides polypeptides and fragments of the extracellular domain that retain a desired biological activity, preferably anti-neoplastic activities (Including altering cytokine and chemokine levels) for which assays for identifying are well known in the art. Such a fragment may be a soluble polypeptide, as described above. In another embodiment, the polypeptides and fragments advantageously include regions that are conserved in the RGL or RTVP family as described above.

Also provided herein are polypeptide fragments comprising at least 20, or at least 30, contiguous amino acids of the sequence of SEQ ID NO: 2, 4, 6, 8 or 10.

Variants

Naturally occurring variants as well as derived variants of the polypeptides and fragments are provided herein. Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA, for example, may also yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (SEQ ID NO: 11), which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG peptide are available from Eastman Kodak Co., Scientific Imaging Systems Division, New Haven, Conn.

Among the variant polypeptides provided herein are variants of native polypeptides that retain the native biological activity or the substantial equivalent thereof One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

Production of Polypeptides and Fragments Thereof

Expression, isolation and purification of the polypeptides and fragments of the invention may be accomplished by any suitable technique, including but not limited to the following:

Expression Systems

The present invention also encompasses recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or other eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides using RNAs derived from DNA constructs disclosed herein.

Isolation and Purification

The invention also includes methods of isolating and purifying the polypeptides and fragments thereof. The "isolated" polypeptides or fragments thereof encompassed by this invention are polypeptides or fragments that are not in an environment identical to an environment in which it or they can be found in nature. The "purified" polypeptides or fragments thereof encompassed by this invention may be essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides, as well as the Fc moieties.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS- PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (Including proteins, polypeptides, fragments, variants, oligomers, and other forms) may be tested for the ability to bind counter-structures/ligands in any suitable assay, such as a conventional binding assay.

Use of RGL2 Nucleic Acid or Oligonucleotides

In addition to being used to express polypeptides as described above, the nucleic acids of the invention, including DNA, and oligonucleotides thereof can be used:
- as probes to identify nucleic acid encoding proteins having anti-neoplastic activities;
- as single-stranded sense or antisense oligonucleotides, to inhibit expression of polypeptide encoded by the RGL2 gene;
- to help detect defective genes in an individual; and
- for preventative and therapeutic measures.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO: 1, 3, 5, 7 or 9 from other mammalian species are contemplated herein, probes based on the human DNA sequence of SEQ ID NO: 1, 3, 5, 7 or 9 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA (SEQ ID NO: 1, 3, 5, 7 or 9). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Preventative and Therapeutic Measures

The invention encompasses the use of RGL2 nucleic acids or fragments thereof in the prevention and treatment of neoplastic disorders. Nucleic acids of the invention may be packaged in a viral vector such as, for example, a retroviral, a vaccinia or an adenoviral vector and used in gene therapy. The invention further includes vectors comprising the nucleic acid sequences of the invention, polypeptides expressed by these vectors, and recombinant cells comprising these vectors.

The invention further provides for the use of RGL2 promoters which modulate transcription (e.g. by differential methylation of promoter sequences) of RGL2 sequences in normal, pre-malignant and malignant cell. These promoters can be functionally coupled to anti-neoplastic genes to treat or prevent cell proliferative disorders such as, for example, tumors, prostate cancer, and metastatic disease.

Nucleic acids and polypeptides of the invention may also be used as a diagnostic or therapeutic tools in the detection, treatment or prevention of diseases, such as neoplastic disorders (e.g. malignant tumors, metastatic disease) and cell or tissue growth disorders. For example the invention encompasses diagnostic; aids or kits for the detection of neoplasia in a patient. Detection kits may comprise RGL2 nucleic acid sequences or polypeptides whose presence or absence in the sample would be indicative of the presence of a disease such as, for example, genitourinary cancer or a genitourinary metastasis, samples which can be analyzed include samples of biological fluids (e.g. blood, plasma, seminal fluid, interstitial fluid, urine, cerebrospinal fluid) and samples of biological tissue (e.g. surgical biopsy). Treatment may involve using the sequences, or effective parts thereof, in gene therapy, including gene ablation, gene expression and gene suppression, such as antisense suppression. Diagnosis may involve genotypic analysis of samples to determine the existence and expression levels of the genes. Nucleic acids of the present invention may be used in various treatment and research modalities, including gene replacement, gene supplementation/over-expression, gene targeting, antisense inhibition, antisense blocking, genetic ablation and gene silencing. Gene replacement involves replacing a copy of a defective gene with another copy by homologous recombination. Gene supplementation involves placing a natively expressed gene under the control of a more prolific promoter system to increase the transcription of the gene as compared to its native state. Gene targeting involves the disruption of a cellular copy of a gene by homologous recombination. Gene targeting refers to a process of introducing a nucleic acid construct into a cell to specifically recombine with a target gene in the cell. The nucleic acid construct inactivates the gene after targeting. Inactivation may be by introduction of termination codons into a coding region or introduction of a repression site into a regulatory sequence. Antisense inhibition exploits the specificity of hybridization reactions between two complementary nucleic acid chains to suppress gene expression. Genetic ablation (gene knockout) may be performed after a cell is selected for use or by selecting a cell already comprising a genotype with the proper genetic ablation. Gene silencing is performed by transfecting cells with nucleic acids which cause genetic ablation or by antisense suppression. The silencing process may include processes such as gene targeting or antisense blocking.

Use of RGL2 Polypeptides and Fragmented Polypeptides
  Uses include, but are not limited to, the following:
  Purifying proteins and measuring activity thereof
  Therapeutic and Research Reagents
  Preparation of Antibodies
  Purification Reagents The polypeptides of the invention finds use as a protein purification reagent. The polypeptides may be attached to a solid support material and used to purify binding partner(s) proteins by affinity chromatography. In particular embodiments, a polypeptide (in any form described herein that is capable of binding to binding partner(s)) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express binding partners (RGL2 ligands) on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing putative RGL2 ligand expressing cells are contacted with the solid phase having the polypeptides thereon. Cells expressing binding partners on the cell surface bind to the fixed polypeptides, and unbound cells then are washed away.

Alternatively, the polypeptides can be conjugated to a detectable moiety, and then incubated with cells to be tested for expression of RGL2 ligands. After incubation, unbound labeled matter is removed and the presence or absence of the detectable moiety on the cells is determined.

In a further alternative, mixtures of cells suspected of containing RGL2 ligand expressing cells are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods.

Measuring Activity

Polypeptides also find use in measuring the biological activity of RGL2 ligands in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a RGL2 ligand that has been stored at different temperatures, or produced in different cell types. The proteins also may be used to determine whether biological activity is retained after modification of a binding partner protein (e.g., chemical modification, truncation, mutation, etc.). The binding affinity of the modified binding partner protein is compared to that of an unmodified protein to detect any adverse impact of the modifications on biological activity of the modified one.

Therapeutic Agents

Polypeptides of the invention may be used in developing treatments for any neoplastic disorder mediated (directly or indirectly) by defective or insufficient amounts of the polypeptides. These polypeptides may be administered to a mammal afflicted with such a neoplastic disorder, especially with regard to prostate cancer.

The polypeptides may also be employed in inhibiting neoplastic biological activities, in in vitro or in vivo procedures. For example, a purified polypeptide may be used to mimic binding to RGL2 ligands on endogenous cell surfaces. Biological effects that result from the binding to endogenous receptors thus are activated.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble RGL2 polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Research Agents

Another embodiment of the invention relates to uses of RGL2 peptides to study cell signal transduction. For example, Apoptosis, a biological activity moderated by RGL2 (FIG. 8), may play a central role in anti-neoplastic biological activities. Alternatively, RGL2 peptides may be used in the search for RGL2 ligands as discussed above.

Another use of the polypeptides of the present invention would be as a research tool for studying anti-neoplastic activities, especially with regard to genitourinary cancers.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatant from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses*, Kennet et al. (eds.), Plenum Press, N.Y. (1980); and *Antibodies: A Laboratory Manual*, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332: 323, 1988), Liu et al. (PNAS 84:3439, 1987), Larrick et al. (*Bio/Technology* 7:934, 1989), and winter and Harris (TIPS 14:139, May, 1993). Procedures to generate antibodies transgenically can be found in GB 2,272,440, U.S. Pat. Nos. 5,569, 825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to RGL2 ligands may be used to inhibit a biological activity that results from such binding. Such blocking antibodies may be identified using any suitable assay procedure, such as by testing antibodies for the ability to inhibit binding of RGL2 peptides to certain cells expressing the binding partner(s). Alternatively, blocking antibodies may be identified in assays for the ability to inhibit a biological effect, such as the induction of apoptosis or the interaction of RGL2 with certain cell types.

Such an antibody may be employed in an in vitro procedure, or administered in vivo to inhibit a biological activity mediated by the entity that generated the antibody. Biological activities caused or exacerbated (directly or indirectly) by the interaction of RGL2 peptides with cell thus may be modulated. A therapeutic method involves in vivo administration of a blocking antibody to a mammal in an amount effective in inhibiting the targeted biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, induce biological effects (e.g., transduction of biological signals) similar to the effects initiated by interactions between the RGL2 peptide and given cell. Agonistic antibodies may be used to induce apoptosis or anti-neoplastic biological activities.

Compositions comprising an antibody with specificity for either an RGL2 peptide or an RGL2 ligand, and a physiologically acceptable diluent, excipient, or carrier, are provided herein.

Also provided herein are conjugates comprising a detectable (e.g., diagnostic) or therapeutic agent, attached to the antibody. Examples of such agents are presented above. The conjugates find use in in vitro or in vivo procedures.

EXAMPLES

The following examples are provided to further illustrate particular embodiments of the invention, and are not to be construed as limiting the scope of the present invention.

Example 1

Isolation and Identification of the RGL2 Nucleic Acid

A cDNA was identified using homology search and PCR-based approaches that corresponded to a reported sequence; accession MGC39497 in the NCBI database. The gene is the second in a family of such genes herein called RTVP-1/GliPR-like (RGL2). There are at least five spliced forms of the human RGL2 mRNA, the sequences of which are presented in FIGS. 1A-E and which are labeled RGL2 α, β, γ, δ, and ε. The genomic structure of the various exons used in the five splice forms of RGL-2 gene are diagrammed in FIG. 3. The proteins encoded by the five splice forms are presented in FIG. 2. FIG. 2 also presents an alignment of the five protein sequences along with a consensus sequence. The RTV P-1/RGL gene family have been mapped to a region of human chromosome 12 and the related mouse gene family to a region of mouse chromosome 10 (FIG. 4).

Example 2

Identification of RGL2 as a p53 Target Gene

The DNA sequences of the RGL2 gene contains various putative consensus p53 binding sites. The RGL2 sequence corresponds to a genomic sequence reported in the NCBI database, accession AC121761, Homo sapiens 12 BAC RP11-585P4. FIG. 5 shows various potential p53 binding sites relative to the various RGL2 exons and introns. Analysis of these sites for p53 binding was performed by functionally linking each such site to a minimal promoter construct. FIG. 5 also shows the relative activities of these synthetic p53 binding sites under the control of such a minimal promoter construct (luciferase normalized to β-gal levels using cotransfection of 148-1 PA mouse prostate cancer cells). This demonstrates that these are functional p53 sites and that transcription of the RGL2 is under full or partial control of p53 acting as a transcription factor. p53-induced genes are associated with cancer progression and metastasis.

Example 3

RGL2 Mediated Induction of Apoptosis in TSUPr1 Cells

Figure 6:
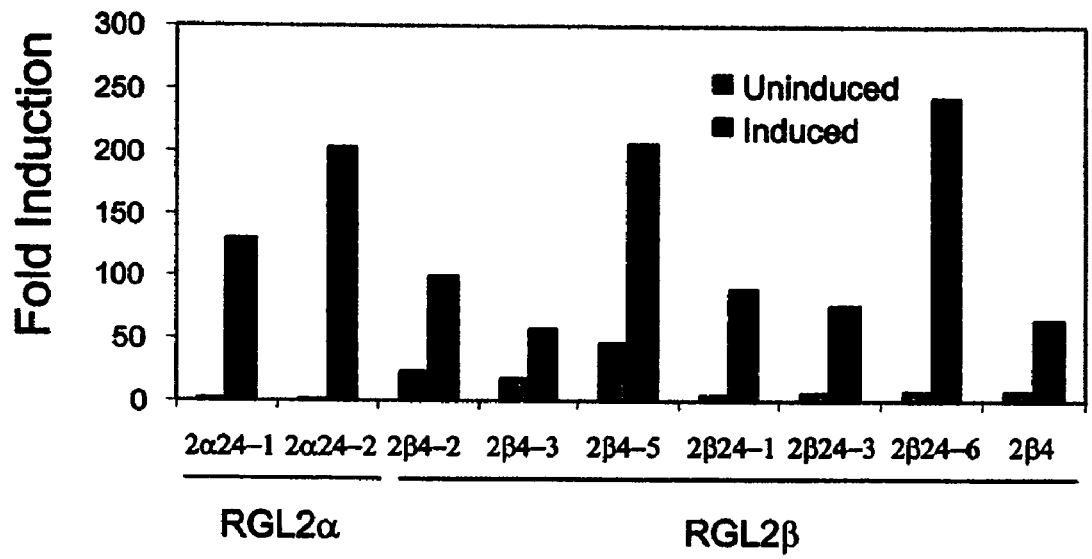
FIG. 6 demonstrates that test constructs designed to control the expression of human RGL2-alpha and RGL2-beta can induce expression of said genes when doxacycline is added for 24-hours.
Figure 7:
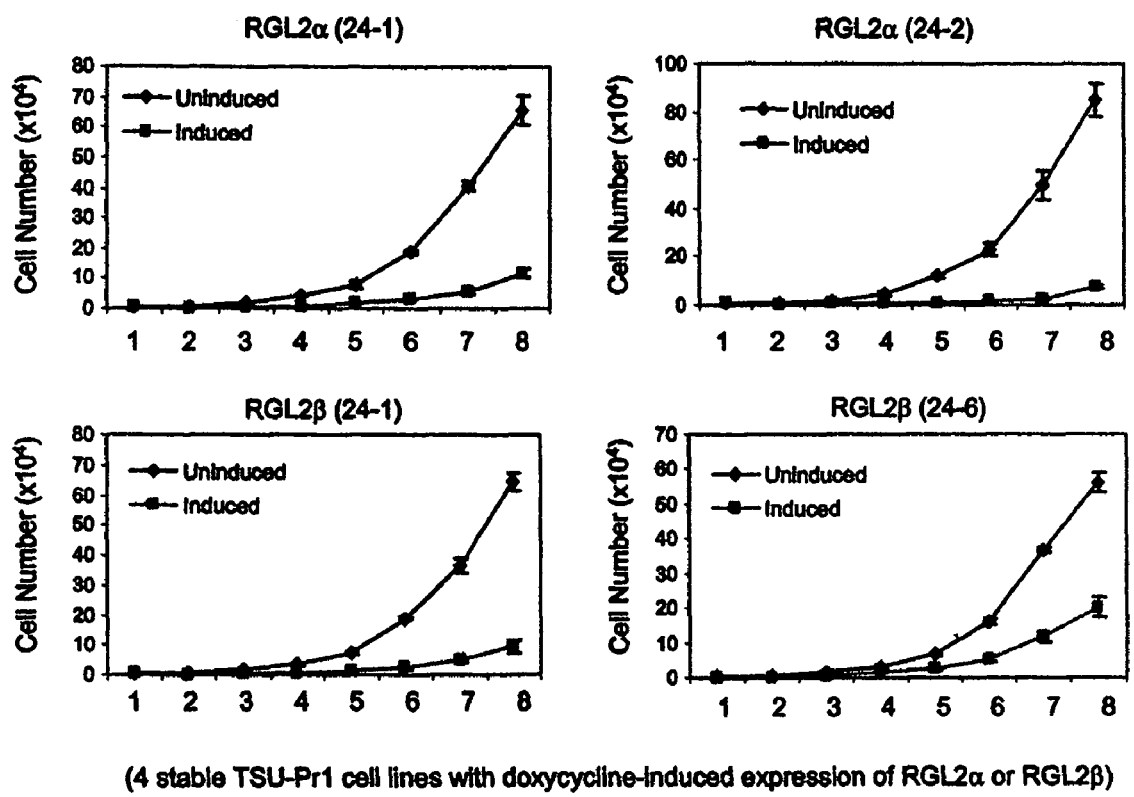
FIG. 7 demonstrates the suppression of cell growth in the TSUPr1 cell line by inducing the expression of the amino acid sequences of RGL2-alpha and RGL2-beta.
Figure 8:
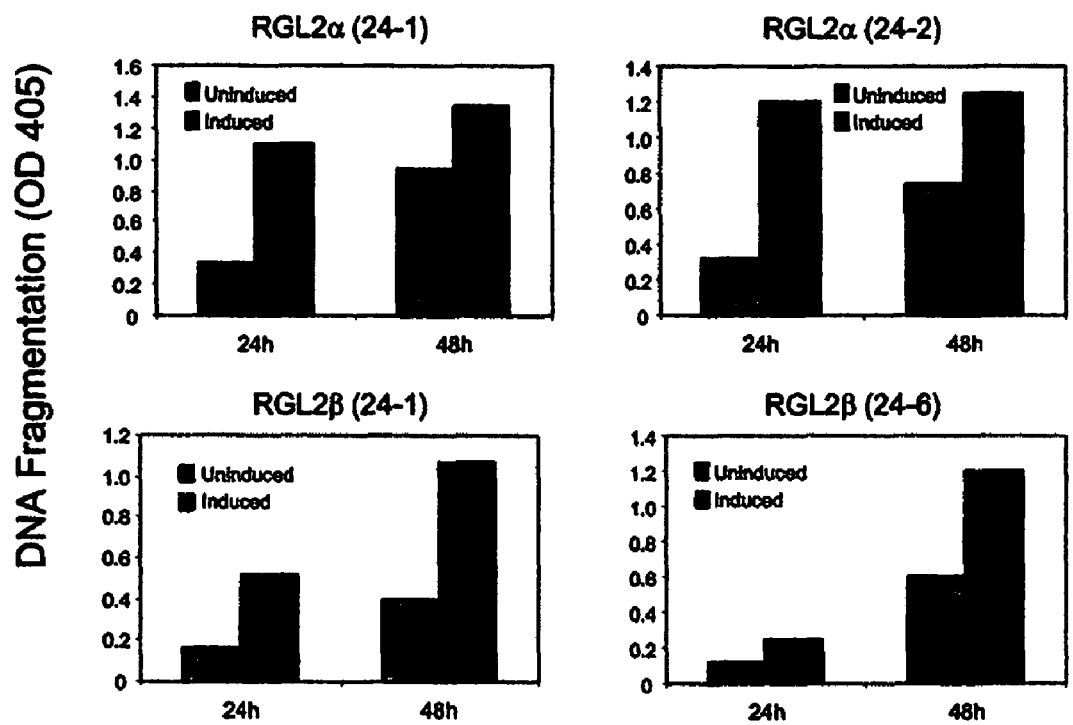
FIG. 8 demonstrates the induction of DNA fragmentation related to apoptosis by inducing expression of the amino acid sequences of RGL2-alpha and RGL2-beta in the TSUPr1 cell line.

Apoptosis related in vitro endpoints were analyzed following stable transfection of TRE-promoter-cDNA constructs into CMV-rtTA TSUPr1 human prostate cancer cells and stimulation with doxacycline. FIG. 6 shows the efficacy of induction by doxacycline for 2 stable RGL2-alpha and 7 stable RGL2-beta clones indicating that several hundred-fold induction of expression occurs. FIG. 7 demonstrates the ability of RGL2-alpha and RGL2-beta to suppress cell proliferation as measured by absolute cell number over time. FIG. 8 shows that RGL2-alpha and RGL2-beta both can induce DNA fragmentation and FIG. 9 shows that RGL2-alpha and RGL2-beta can suppress the colony-forming ability of a cancer cell line. All these parameters are consistent with the ability of RGL2, like RTVP-1 and RGLI, to induce apoptosis and cell killing in a cancer cell line.

Example 4

Hypermethylation and Reduced Expression of RGL2 in Cancer Patients

Normal and tumor tissues from two prostate cancer patients were tested for expression of RGL2 and examined for the degree of hypermethylation of the RGL2 promoters. FIG. 10A demonstrates that RGL2 expression is decreased in tumor tissue as compared to normal tissue from the same patient. This reduction in expression is correlated with an increase in the percent of CpG islands that are methylated in the RGL2 promoters and shown in FIG. 10B. These results indicate that established and developing cancers such as prostate cancer in some cases require that RGL2 be down-regulated in order for the anti-tumor activity of RGL2 peptides to be circumvented. This suggests a therapeutic avenue to treat cancers by replacing RGL2 peptides in the patient.

Example 5

RGL2 Mediated Regulation of Cytokines and Chemokines

The ability of RGL2-alpha and RGL2-beta to induce expression of cytokines and chemokines in cultured THP1 monocytes is presented in FIG. 11. Antibodies selective for various cytokines and chemokines are arrayed on blots which are then incubated with media from cultured THP1 monocytes expressing RTVP-family genes via infection with engineered adenoviral vectors. β-gal is a control adenoviral vector expressing bacterial beta-galactosidase and p144 is the mouse RTVP-1 protein. When monocytes are expressing RGL2-alpha or RGL2-beta the IL-6, IL-8 and IL-lb cytokines and the GRO chemokine are up-regulated. This response reflects the stimulation of the antigen-presenting function of the immune system in order to generate an anti-tumor response. Dendritic cell viability, maturation and differentiation are controlled by RTVP-family member proteins and in the context of advancing and metastatic prostate cancer, is crucial for a robust anti-tumor response.

Example 6

RGL2 is Expressed in Testes, Prostate, Kidney and Bone Marrow

RGL2 expression was tested in various tissues by quantitative-PCR. FIG. 12 shows the results from this analysis. The highest expression is seen in testes with significant expression also seen in prostate, kidney and bone marrow. The presence of RGL2 expression in testes along with the known role of the gene in apoptosis, cancer progression, tumor killing and stimulation of the immune response means RGL2 is involved in crucial functions of the urogenital system. Such a function might include, but not be limited to, fertility. RTVP-family genes are also known to be involved in the function of the immune system specifically, but not necessarily limited to, the function of the antigen presenting system represented by dendritic cells and macrophages. Expression of RGL2 in the bone marrow is consistent with RGL2 sharing the immune system function known for other RTVP-family member genes.

Example 7

RTVP-Family Mediated In Vivo Tumor Killing

Figure 13:
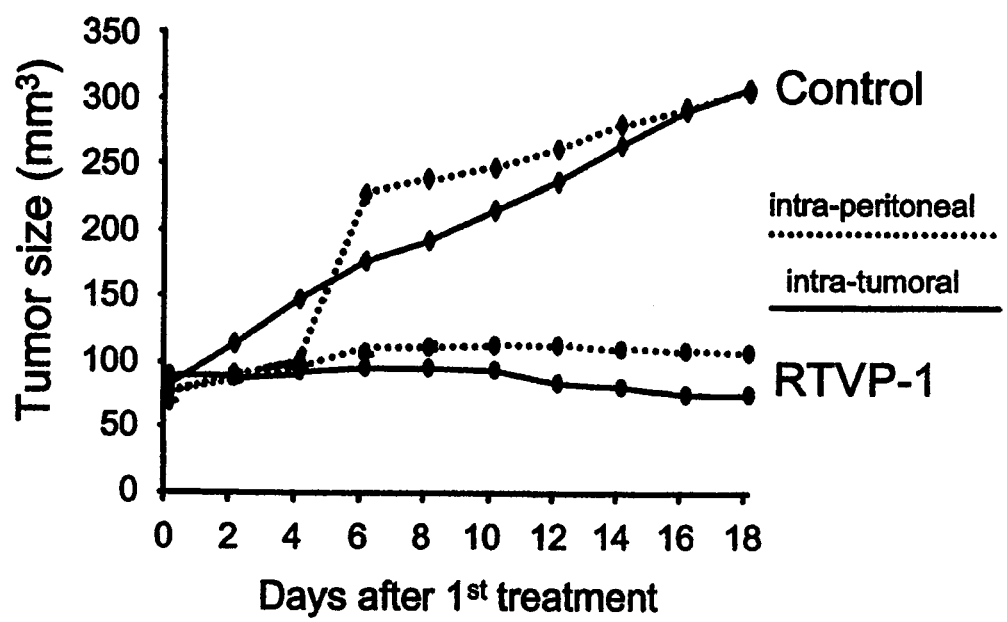
FIG. 13 demonstrates that RTV P-1 protein can stop xenograft tumors growing in nude mice by either injecting the protein into the tumor or intra-peritoneally. RTVP-1 is related to the RGL2 gene and shares its other properties.

The RTVP-family protein, RTVP-1, can reduce and kill tumor cells in an in vivo model of cancer. RTVP-1 shares the features of RGL2 presented in the previous examples including regulation by p53, the ability to induce apoptosis, down-regulation by methylation in tumor cells and the involvement in the immune response to tumors. FIG. 13 shows how purified RTVP-1 protein stops the growth of tumors in an animal model. Human prostate cancer cells were injected into a nude mouse and allowed to form tumors of approximately 75-mm$^3$. Animals were treated by injection of a control unrelated peptide or RTVP-1 purified protein (2-µg every 2 days) either intra-peritoneally or intra-tumorally. By either route of administration, the tumors in the experimental group did not grow like the tumors treated with a control peptide. Over the course of 3 weeks, the RTV P-1-treated tumors were even beginning to shrink.

What is claimed is:

1. An isolated polypeptide encoded by a nucleic acid molecule selected from:
   (a) the DNA sequence of SEQ ID NO:1, SEQ ID NO:3, SEQ ID NO:5, SEQ ID NO:7 or SEQ ID NO:9;
   (b) an isolated nucleic acid molecule encoding an amino acid sequence comprising the sequence of SEQ ID NO:2, SEQ ID NO:4, SEQ ID NO:6, SEQ ID NO:8, or SEQ ID NO:10; or
   (c) an isolated nucleic acid molecule degenerate from SEQ ID NO:1, SEQ ID NO:3, SEQ ID NO:5, SEQ ID NO:7 or SEQ ID NO:9 as a result of the genetic code.

2. The polypeptide of claim 1 wherein the polypeptide is capable of inducing apoptosis in neoplastic cells.

3. The polypeptide of claim 1 wherein the polypeptide has an anti-neoplastic activity.

4. The polypeptide of claim 1 in a composition comprising a pharmaceutically acceptable carrier selected from the group consisting of water, oils, alcohols, salts, fatty acids, saccharides, polysaccharides and combinations thereof.

5. An isolated RGL2 receptor protein or portion thereof which binds to the polypeptide of claim 1.

6. A method for treating a patient for a neoplastic disorder comprising administering to the patient a therapeutically effective amount of a composition comprising at least an active portion of the polypeptide of claim 1 having anti-neoplastic activity.

7. The method of claim 6 wherein the anti-neoplastic activity is a modulation of chemokine expression.

8. The method of claim 6 wherein the anti-neoplastic activity is a modulation of cytokine expression.

9. The method of claim 6 wherein the therapeutically effective amount of the composition is administered locally to a tumor site, systemically, or parenterally.

10. The method of claim 6, comprising administering an adenoviral vector that expresses the polypeptide.

11. The method of claim 6, wherein the metastatic disorder is prostate cancer.

* * * * *

```
                        SEQUENCE LISTING

<160> NUMBER OF SEQ ID NOS: 11

<210> SEQ ID NO 1
<211> LENGTH: 1746
<212> TYPE: DNA
<213> ORGANISM: Homosapiens
<220> FEATURE:
<221> NAME/KEY: CDS
<222> LOCATION: (9)..(767)

<400> SEQUENCE: 1 ggtgaacc atg gag gcc gca agg ccc ttc gcc cgg gag tgg agg gcc cag        50
         Met Glu Ala Ala Arg Pro Phe Ala Arg Glu Trp Arg Ala Gln
          1               5                  10 tcc cta ccc ctg gca gta ggg ggc gtt ttg aag ctg cgg ctc tgt gag         98
Ser Leu Pro Leu Ala Val Gly Gly Val Leu Lys Leu Arg Leu Cys Glu
15                  20                  25                  30 ctg tgg cta ctg cta ctg ggt tct agt ttg aac gcc aga ttt ttg cca        146
Leu Trp Leu Leu Leu Leu Gly Ser Ser Leu Asn Ala Arg Phe Leu Pro
                35                  40                  45 gac gag gag gac gta gac ttt atc aac gag tac gtg aac ctc cac aat        194
Asp Glu Glu Asp Val Asp Phe Ile Asn Glu Tyr Val Asn Leu His Asn
            50                  55                  60 gag ctg cgg ggc gac gtc att ccc cga ggg tct aac ttg cgc ttc atg        242
Glu Leu Arg Gly Asp Val Ile Pro Arg Gly Ser Asn Leu Arg Phe Met
        65                  70                  75 act tgg gat gta gct tta tca cgg act gct aga gca tgg gga aaa aaa        290
Thr Trp Asp Val Ala Leu Ser Arg Thr Ala Arg Ala Trp Gly Lys Lys
    80                  85                  90 tgt ttg ttt acg cat aat att tat tta caa gat gta caa atg gtc cat        338
Cys Leu Phe Thr His Asn Ile Tyr Leu Gln Asp Val Gln Met Val His
95                  100                 105                 110 cct aaa ttt tat ggt att ggt gaa aat atg tgg gtc ggc cct gaa aat        386
Pro Lys Phe Tyr Gly Ile Gly Glu Asn Met Trp Val Gly Pro Glu Asn
                115                 120                 125
```

```
gaa ttt act gca agt att gct atc aga agt tgg cat gca gag aag aaa      434
Glu Phe Thr Ala Ser Ile Ala Ile Arg Ser Trp His Ala Glu Lys Lys
            130                 135                 140 atg tac aat ttt gaa aat ggc agt tgc tct gga gac tgt tct aat tat      482
Met Tyr Asn Phe Glu Asn Gly Ser Cys Ser Gly Asp Cys Ser Asn Tyr
145                 150                 155 att cag ctt gtt tgg gac cac tct tac aaa gtt ggt tgt gct gtt act      530
Ile Gln Leu Val Trp Asp His Ser Tyr Lys Val Gly Cys Ala Val Thr
    160                 165                 170 cca tgt tca aaa att gga cat att ata cat gca gca att ttc ata tgc      578
Pro Cys Ser Lys Ile Gly His Ile Ile His Ala Ala Ile Phe Ile Cys
175                 180                 185                 190 aac tat gcg cca gga gga aca ctg acg aga aga cct tat gaa cca gga      626
Asn Tyr Ala Pro Gly Gly Thr Leu Thr Arg Arg Pro Tyr Glu Pro Gly
                195                 200                 205 ata ttt tgt act cga tgt ggc aga cgt gac aaa tgc aca gat ttt cta      674
Ile Phe Cys Thr Arg Cys Gly Arg Arg Asp Lys Cys Thr Asp Phe Leu
            210                 215                 220 tgc agt aag ata aag aaa ata aac atg aaa aaa atg cat aat gga ttg      722
Cys Ser Lys Ile Lys Lys Ile Asn Met Lys Lys Met His Asn Gly Leu
                225                 230                 235 gac aag aaa aat aag cga ttg aac act agt ttt tta tgg tca tgt          767
Asp Lys Lys Asn Lys Arg Leu Asn Thr Ser Phe Leu Trp Ser Cys
240                 245                 250 taatattatt cctttgatca gaatgctact attatgttat caaaggatgg ttgacacagt    827
atcatcttta gattttccta aactgcagag ctttttctgt tctatcttaa ccctattcct    887
tcccctgagg acataccaga gtgtcagaaa gaaagaatga gaactaacag ttataccctt    947
aaaaagcttc acagtttatg cccaaacagc agcctgtttg ataataactg ctttaaagga   1007
tagtatattc caaaatattt atgaagtagc atatatttaa tacccttttc ttttagtttt   1067
tcctccaaaa agctgaaatc tccaaatatt tcaaaagtaa aaagtagaaa atatgtttga   1127
ttacattttt cttttagttt ttccaaacat gagagaatat actccaaaag tataactgta   1187
gctaaaatat acaatgctta gaggaatatg gtaggagata aatttggata ataagtaaat   1247
agcatattat gttgtttttt aattattata ctttaagttc tggggtacct gtgcagaacg   1307
tgcaggtttg ttacataggt atatacatgc catggtggtt tgctgcaccc atgaacccat   1367
catctacatt agatatttct cctaagctat tcctccccta gccctgaccc cctgacaggc   1427
cccagtgtgt gatgttcttc tccctgtgtc catgtgttct cattgttcaa ctcccactta   1487
tgagtgagaa catgcagtgt ttggttttct gttcttgtga tagtttgctg agaatgatgg   1547
tttgcagctt catccatgtc cctgaaaagg aaatgaactc atccttttt atggctgcat    1607
agtattccat ggtgtatatg tgccacactt tctttatcca gtctatcatt gatgggcgtt   1667
tgggttggtt ccaagtattt gctattgtga acagtgctgc aataaacata tgtttgcagg   1727
tgaaaaaaaa aaaaaaaa                                                 1746
```

<210> SEQ ID NO 2
<211> LENGTH: 253
<212> TYPE: PRT
<213> ORGANISM: Homosapiens

<400> SEQUENCE: 2

```
Met Glu Ala Ala Arg Pro Phe Ala Arg Glu Trp Arg Ala Gln Ser Leu
1               5                   10                  15

Pro Leu Ala Val Gly Gly Val Leu Lys Leu Arg Leu Cys Glu Leu Trp
            20                  25                  30
```

```
Leu Leu Leu Leu Gly Ser Ser Leu Asn Ala Arg Phe Leu Pro Asp Glu
            35                  40                  45

Glu Asp Val Asp Phe Ile Asn Glu Tyr Val Asn Leu His Asn Glu Leu
 50                  55                  60

Arg Gly Asp Val Ile Pro Arg Gly Ser Asn Leu Arg Phe Met Thr Trp
 65                  70                  75                  80

Asp Val Ala Leu Ser Arg Thr Ala Arg Ala Trp Gly Lys Lys Cys Leu
                 85                  90                  95

Phe Thr His Asn Ile Tyr Leu Gln Asp Val Gln Met Val His Pro Lys
            100                 105                 110

Phe Tyr Gly Ile Gly Glu Asn Met Trp Val Gly Pro Glu Asn Glu Phe
            115                 120                 125

Thr Ala Ser Ile Ala Ile Arg Ser Trp His Ala Glu Lys Lys Met Tyr
            130                 135                 140

Asn Phe Glu Asn Gly Ser Cys Ser Gly Asp Cys Ser Asn Tyr Ile Gln
145                 150                 155                 160

Leu Val Trp Asp His Ser Tyr Lys Val Gly Cys Ala Val Thr Pro Cys
                165                 170                 175

Ser Lys Ile Gly His Ile Ile His Ala Ala Ile Phe Ile Cys Asn Tyr
            180                 185                 190

Ala Pro Gly Gly Thr Leu Thr Arg Arg Pro Tyr Glu Pro Gly Ile Phe
            195                 200                 205

Cys Thr Arg Cys Gly Arg Arg Asp Lys Cys Thr Asp Phe Leu Cys Ser
210                 215                 220

Lys Ile Lys Lys Ile Asn Met Lys Lys Met His Asn Gly Leu Asp Lys
225                 230                 235                 240

Lys Asn Lys Arg Leu Asn Thr Ser Phe Leu Trp Ser Cys
                245                 250

<210> SEQ ID NO 3
<211> LENGTH: 1390
<212> TYPE: DNA
<213> ORGANISM: Homosapiens
<220> FEATURE:
<221> NAME/KEY: CDS
<222> LOCATION: (121)..(957)

<400> SEQUENCE: 3
atctcgggta gttggggcca ctgctctgag gctgaaggat cgcggagaac cgcactttta      60
gcttggtttt taaagtacac gtgaagttta cacagagaaa aactgcggac actctaacac     120 atg ctt att acc atg ata tta cac agg gcc agg act aag act tgg gat      168
Met Leu Ile Thr Met Ile Leu His Arg Ala Arg Thr Lys Thr Trp Asp
 1               5                  10                  15 gta gct tta tca cgg act gct aga gca tgg gga aaa aaa tgt ttg ttt      216
Val Ala Leu Ser Arg Thr Ala Arg Ala Trp Gly Lys Lys Cys Leu Phe
                20                  25                  30 acg cat aat att tat tta caa gat gta caa atg gtc cat cct aaa ttt      264
Thr His Asn Ile Tyr Leu Gln Asp Val Gln Met Val His Pro Lys Phe
            35                  40                  45 tat ggt att ggt gaa aat atg tgg gtc ggc cct gaa aat gaa ttt act      312
Tyr Gly Ile Gly Glu Asn Met Trp Val Gly Pro Glu Asn Glu Phe Thr
         50                  55                  60 gca agt att gct atc aga agt tgg cat gca gag aag aaa atg tac aat      360
Ala Ser Ile Ala Ile Arg Ser Trp His Ala Glu Lys Lys Met Tyr Asn
 65                  70                  75                  80 ttt gaa aat ggc agt tgc tct gga gac tgt tct aat tat att cag ctt      408
```

-continued

| | | |
|---|---|---|
| gtt tgg gac cac tct tac aaa gtt ggt tgt gct gtt act cca tgt tca<br>Val Trp Asp His Ser Tyr Lys Val Gly Cys Ala Val Thr Pro Cys Ser<br>100 105 110 | | 456 |
| aaa att gga cat att ata cat gca gca att ttc ata tgc aac tat gcg<br>Lys Ile Gly His Ile Ile His Ala Ala Ile Phe Ile Cys Asn Tyr Ala<br>115 120 125 | | 504 |
| cca gga gga aca ctg acg aga aga cct tat gaa cca gga ata ttt tgt<br>Pro Gly Gly Thr Leu Thr Arg Arg Pro Tyr Glu Pro Gly Ile Phe Cys<br>130 135 140 | | 552 |
| act cga tgt ggc aga cgt gac aaa tgc aca gat ttt cta tgc agt aat<br>Thr Arg Cys Gly Arg Arg Asp Lys Cys Thr Asp Phe Leu Cys Ser Asn<br>145 150 155 160 | | 600 |
| gca gat cgt gac caa gcc aca tat tac cga ttt tgg tat cca aaa tgg<br>Ala Asp Arg Asp Gln Ala Thr Tyr Tyr Arg Phe Trp Tyr Pro Lys Trp<br>165 170 175 | | 648 |
| gaa atg ccc cgg cca gtt gtg tgt gat cca ctg tgc aca ttc att tta<br>Glu Met Pro Arg Pro Val Val Cys Asp Pro Leu Cys Thr Phe Ile Leu<br>180 185 190 | | 696 |
| tta ttg aga ata tta tgt ttt atc ctg tgt gtc ata act gtt ttg ata<br>Leu Leu Arg Ile Leu Cys Phe Ile Leu Cys Val Ile Thr Val Leu Ile<br>195 200 205 | | 744 |
| gta cag tct cag ttt cca aat atc ttg ttg gaa caa caa atg ata ttt<br>Val Gln Ser Gln Phe Pro Asn Ile Leu Leu Glu Gln Gln Met Ile Phe<br>210 215 220 | | 792 |
| acc cct gag gaa tct gaa gca ggg aat gaa gag gag gaa aaa gag gaa<br>Thr Pro Glu Glu Ser Glu Ala Gly Asn Glu Glu Glu Lys Glu Glu<br>225 230 235 240 | | 840 |
| gag aag aaa gag aaa gag gaa atg gaa atg gaa ata atg gaa atg gag<br>Glu Lys Lys Glu Lys Glu Glu Met Glu Met Glu Ile Met Glu Met Glu<br>245 250 255 | | 888 |
| gag gaa aaa gaa gag aga gag gag gag gag gaa aca caa aaa gaa<br>Glu Glu Lys Glu Glu Arg Glu Glu Glu Glu Glu Thr Gln Lys Glu<br>260 265 270 | | 936 |
| aag atg gag gaa gag gaa aaa taagagtaga aagaggagga aaaagatgta<br>Lys Met Glu Glu Glu Glu Lys<br>275 | | 987 |
| tcaccaatat aaaccaaaag tgtaatacaa aaaagacag aaaaaaaaaa aaagtaaaac | | 1047 |
| actgagtttt aacaagaaag aaaatatgca aaccaccatt ggaatgtttt ttattcccctt | | 1107 |
| ctctcctata cttattcaat caatttaaat ttgtaaaaca aagaaacaaa aaacatgtaa | | 1167 |
| ggtgggctct tgacactaa gaacagataa agacatgaca ggaaaaacac tgaaaaacat | | 1227 |
| ttgaccagtc taattaatct taagatttca ccatgttatt ctaataaagt agggaatttt | | 1287 |
| cattttctaa acatgtttcc atctctgtgt tttaaatagt aaggtgctta agatcattcc | | 1347 |
| aagttcataa caaccattga ataaaatttg tatttttttg ttt | | 1390 |

<210> SEQ ID NO 4
<211> LENGTH: 279
<212> TYPE: PRT
<213> ORGANISM: Homosapiens

<400> SEQUENCE: 4

Met Leu Ile Thr Met Ile Leu His Arg Ala Arg Thr Lys Thr Trp Asp
1               5                   10                  15

Val Ala Leu Ser Arg Thr Ala Arg Ala Trp Gly Lys Lys Cys Leu Phe
            20                  25                  30

```
Thr His Asn Ile Tyr Leu Gln Asp Val Gln Met Val His Pro Lys Phe
        35                  40                  45

Tyr Gly Ile Gly Glu Asn Met Trp Val Gly Pro Glu Asn Glu Phe Thr
 50                  55                  60

Ala Ser Ile Ala Ile Arg Ser Trp His Ala Glu Lys Lys Met Tyr Asn
 65                  70                  75                  80

Phe Glu Asn Gly Ser Cys Ser Gly Asp Cys Ser Asn Tyr Ile Gln Leu
                 85                  90                  95

Val Trp Asp His Ser Tyr Lys Val Gly Cys Ala Val Thr Pro Cys Ser
            100                 105                 110

Lys Ile Gly His Ile Ile His Ala Ala Ile Phe Ile Cys Asn Tyr Ala
            115                 120                 125

Pro Gly Gly Thr Leu Thr Arg Arg Pro Tyr Glu Pro Gly Ile Phe Cys
        130                 135                 140

Thr Arg Cys Gly Arg Arg Asp Lys Cys Thr Asp Phe Leu Cys Ser Asn
145                 150                 155                 160

Ala Asp Arg Asp Gln Ala Thr Tyr Tyr Arg Phe Trp Tyr Pro Lys Trp
                165                 170                 175

Glu Met Pro Arg Pro Val Val Cys Asp Pro Leu Cys Thr Phe Ile Leu
            180                 185                 190

Leu Leu Arg Ile Leu Cys Phe Ile Leu Cys Val Ile Thr Val Leu Ile
        195                 200                 205

Val Gln Ser Gln Phe Pro Asn Ile Leu Leu Glu Gln Gln Met Ile Phe
    210                 215                 220

Thr Pro Glu Glu Ser Glu Ala Gly Asn Glu Glu Glu Lys Glu Glu
225                 230                 235                 240

Glu Lys Lys Glu Lys Glu Glu Met Glu Met Glu Ile Met Glu Met Glu
                245                 250                 255

Glu Glu Lys Glu Glu Arg Glu Glu Glu Glu Glu Thr Gln Lys Glu
            260                 265                 270

Lys Met Glu Glu Glu Glu Lys
        275

<210> SEQ ID NO 5
<211> LENGTH: 1090
<212> TYPE: DNA
<213> ORGANISM: Homosapiens
<220> FEATURE:
<221> NAME/KEY: CDS
<222> LOCATION: (282)..(992)

<400> SEQUENCE: 5
cactggcctg tcagcggccg gtggaccatg gaggccgcaa ggcccttcgc ccgggagtgg      60
agggcccagt ccctaccect ggcagtaggg ggcgttttga agctgcggct ctgtgagctg     120
tggctactgc tactgggttc tagtttgaac gccagatttt tgccagacga ggaggacgta     180
gactttatca acgaacttgg gatgtagctt tatcacggac tgctagagca tggggaaaaa     240
aatgtttgtt tacgcataat atttatttac aagatgtaca a atg gtc cat cct aaa     296
                                              Met Val His Pro Lys
                                                1               5 ttt tat ggt att ggt gaa aat atg tgg gtc ggc cct gaa aat gaa ttt     344
Phe Tyr Gly Ile Gly Glu Asn Met Trp Val Gly Pro Glu Asn Glu Phe
                10                  15                  20 act gca agt att gct atc aga agt tgg cat gca gag aag aaa atg tac     392
Thr Ala Ser Ile Ala Ile Arg Ser Trp His Ala Glu Lys Lys Met Tyr
            25                  30                  35
```

-continued

```
aat ttt gaa aat ggc agt tgc tct gga gac tgt tct aat tat att cag      440
Asn Phe Glu Asn Gly Ser Cys Ser Gly Asp Cys Ser Asn Tyr Ile Gln
         40                  45                  50 ctt gtt tgg gac cac tct tac aaa gtt ggt tgt gct gtt act cca tgt      488
Leu Val Trp Asp His Ser Tyr Lys Val Gly Cys Ala Val Thr Pro Cys
 55                  60                  65 tca aaa att gga cat att ata cat gca gca att ttc ata tgc aac tat      536
Ser Lys Ile Gly His Ile Ile His Ala Ala Ile Phe Ile Cys Asn Tyr
 70                  75                  80                  85 gcg cca gga gga aca ctg acg aga aga cct tat gaa cca gga ata ttt      584
Ala Pro Gly Gly Thr Leu Thr Arg Arg Pro Tyr Glu Pro Gly Ile Phe
                 90                  95                 100 tgt act cga tgt ggc aga cgt gac aaa tgc aca gat ttt cta tgc agt      632
Cys Thr Arg Cys Gly Arg Arg Asp Lys Cys Thr Asp Phe Leu Cys Ser
            105                 110                 115 aat gca gat cgt gac caa gcc aca tat tac cga ttt tgg tat cca aaa      680
Asn Ala Asp Arg Asp Gln Ala Thr Tyr Tyr Arg Phe Trp Tyr Pro Lys
        120                 125                 130 tgg gaa atg ccc cgg cca gtt gtg tgt gat cca ctg tgc aca ttc att      728
Trp Glu Met Pro Arg Pro Val Val Cys Asp Pro Leu Cys Thr Phe Ile
135                 140                 145 tta tta ttg aga ata tta tgt ttt atc ctg tgt gtc ata act gtt ttg      776
Leu Leu Leu Arg Ile Leu Cys Phe Ile Leu Cys Val Ile Thr Val Leu
150                 155                 160                 165 ata gta cag tct cag ttt cca aat atc ttg ttg gaa caa caa atg ata      824
Ile Val Gln Ser Gln Phe Pro Asn Ile Leu Leu Glu Gln Gln Met Ile
            170                 175                 180 ttt acc cct gag gaa tct gaa gca ggg aat gaa gag gag aaa gag          872
Phe Thr Pro Glu Glu Ser Glu Ala Gly Asn Glu Glu Glu Lys Glu
        185                 190                 195 gaa gag aag aaa gag aaa gag gaa atg gaa atg gaa ata atg gaa atg      920
Glu Glu Lys Lys Glu Lys Glu Glu Met Glu Met Glu Ile Met Glu Met
    200                 205                 210 gag gag gaa aaa gaa gag aga gag gag gag gag gag gaa aca caa aaa      968
Glu Glu Glu Lys Glu Glu Arg Glu Glu Glu Glu Glu Thr Gln Lys
215                 220                 225 gaa aag atg gag gaa gag gaa aaa taagagtaga aagaggagga aaaagatgta   1022
Glu Lys Met Glu Glu Glu Glu Lys
230                 235 tcaccaatat aaaccaaaag tgtaatccaa aaaggccaa aaaaaaaaa aaaaaaaaa     1082 aaaaaaaa                                                            1090
```

<210> SEQ ID NO 6
<211> LENGTH: 237
<212> TYPE: PRT
<213> ORGANISM: Homosapiens

<400> SEQUENCE: 6

Met Val His Pro Lys Phe Tyr Gly Ile Gly Glu Asn Met Trp Val Gly
1               5                   10                  15

Pro Glu Asn Glu Phe Thr Ala Ser Ile Ala Ile Arg Ser Trp His Ala
            20                  25                  30

Glu Lys Lys Met Tyr Asn Phe Glu Asn Gly Ser Cys Ser Gly Asp Cys
        35                  40                  45

Ser Asn Tyr Ile Gln Leu Val Trp Asp His Ser Tyr Lys Val Gly Cys
    50                  55                  60

Ala Val Thr Pro Cys Ser Lys Ile Gly His Ile Ile His Ala Ala Ile
65                  70                  75                  80

```
Phe Ile Cys Asn Tyr Ala Pro Gly Gly Thr Leu Thr Arg Arg Pro Tyr
                 85                  90                  95

Glu Pro Gly Ile Phe Cys Thr Arg Cys Gly Arg Arg Asp Lys Cys Thr
            100                 105                 110

Asp Phe Leu Cys Ser Asn Ala Asp Arg Asp Gln Ala Thr Tyr Tyr Arg
        115                 120                 125

Phe Trp Tyr Pro Lys Trp Glu Met Pro Arg Pro Val Val Cys Asp Pro
    130                 135                 140

Leu Cys Thr Phe Ile Leu Leu Arg Ile Leu Cys Phe Ile Leu Cys
145                 150                 155                 160

Val Ile Thr Val Leu Ile Val Gln Ser Gln Phe Pro Asn Ile Leu Leu
                165                 170                 175

Glu Gln Gln Met Ile Phe Thr Pro Glu Glu Ser Glu Ala Gly Asn Glu
            180                 185                 190

Glu Glu Glu Lys Glu Glu Glu Lys Lys Glu Lys Glu Glu Met Glu Met
        195                 200                 205

Glu Ile Met Glu Met Glu Glu Lys Glu Glu Arg Glu Glu Glu Glu
    210                 215                 220

Glu Glu Thr Gln Lys Glu Lys Met Glu Glu Glu Lys
225                 230                 235

<210> SEQ ID NO 7
<211> LENGTH: 1249
<212> TYPE: DNA
<213> ORGANISM: Homosapiens
<220> FEATURE:
<221> NAME/KEY: CDS
<222> LOCATION: (9)..(1040)

<400> SEQUENCE: 7 ggtgaacc atg gag gcc gca agg ccc ttc gcc cgg gag tgg agg gcc cag        50
         Met Glu Ala Ala Arg Pro Phe Ala Arg Glu Trp Arg Ala Gln
         1               5                   10 tcc cta ccc ctg gca gta ggg ggc gtt ttg aag ctg cgg ctc tgt gag        98
Ser Leu Pro Leu Ala Val Gly Gly Val Leu Lys Leu Arg Leu Cys Glu
15                  20                  25                  30 ctg tgg cta ctg cta ctg ggt tct agt ttg aac gcc aga ttt ttg cca       146
Leu Trp Leu Leu Leu Leu Gly Ser Ser Leu Asn Ala Arg Phe Leu Pro
                35                  40                  45 gac gag gag gac gta gac ttt atc aac gag tac gtg aac ctc cac aat       194
Asp Glu Glu Asp Val Asp Phe Ile Asn Glu Tyr Val Asn Leu His Asn
            50                  55                  60 gag ctg cgg ggc gac gtc att ccc cga ggg tct aac ttg cgc ttc atg       242
Glu Leu Arg Gly Asp Val Ile Pro Arg Gly Ser Asn Leu Arg Phe Met
        65                  70                  75 act tgg gat gta gct tta tca cgg act gct aga gca tgg gga aaa aaa       290
Thr Trp Asp Val Ala Leu Ser Arg Thr Ala Arg Ala Trp Gly Lys Lys
    80                  85                  90 tgt ttg ttt acg cat aat att tat tta caa gat gta caa atg gtc cat       338
Cys Leu Phe Thr His Asn Ile Tyr Leu Gln Asp Val Gln Met Val His
95                  100                 105                 110 cct aaa ttt tat ggt att ggt gaa aat atg tgg gtc ggc cct gaa aat       386
Pro Lys Phe Tyr Gly Ile Gly Glu Asn Met Trp Val Gly Pro Glu Asn
                115                 120                 125 gaa ttt act gca agt att gct atc aga agt tgg cat gca gag aag aaa       434
Glu Phe Thr Ala Ser Ile Ala Ile Arg Ser Trp His Ala Glu Lys Lys
            130                 135                 140 atg tac aat ttt gaa aat ggc agt tgc tct gga gac tgt tct aat tat       482
Met Tyr Asn Phe Glu Asn Gly Ser Cys Ser Gly Asp Cys Ser Asn Tyr
```

-continued

```
                    145                 150                 155
att cag ctt gtt tgg gac cac tct tac aaa gtt ggt tgt gct gtt act    530
Ile Gln Leu Val Trp Asp His Ser Tyr Lys Val Gly Cys Ala Val Thr
        160                 165                 170 cca tgt tca aaa att gga cat att ata cat gca gca att ttc ata tgc    578
Pro Cys Ser Lys Ile Gly His Ile Ile His Ala Ala Ile Phe Ile Cys
175                 180                 185                 190 aac tat gcg cca gga gga aca ctg acg aga aga cct tat gaa cca gga    626
Asn Tyr Ala Pro Gly Gly Thr Leu Thr Arg Arg Pro Tyr Glu Pro Gly
                195                 200                 205 ata ttt tgt act cga tgt ggc aga cgt gac aaa tgc aca gat ttt cta    674
Ile Phe Cys Thr Arg Cys Gly Arg Arg Asp Lys Cys Thr Asp Phe Leu
            210                 215                 220 tgc agt aat gca gat cgt gac caa gcc aca tat tac cga ttt tgg tat    722
Cys Ser Asn Ala Asp Arg Asp Gln Ala Thr Tyr Tyr Arg Phe Trp Tyr
        225                 230                 235 cca aaa tgg gaa atg ccc cgg cca gtt gtg tgt gat cca ctg tgc aca    770
Pro Lys Trp Glu Met Pro Arg Pro Val Val Cys Asp Pro Leu Cys Thr
    240                 245                 250 ttc att tta tta ttg aga ata tta tgt ttt atc ctg tgt gtc ata act    818
Phe Ile Leu Leu Leu Arg Ile Leu Cys Phe Ile Leu Cys Val Ile Thr
255                 260                 265                 270 gtt ttg ata gta cag tct cag ttt cca aat atc ttg ttg gaa caa caa    866
Val Leu Ile Val Gln Ser Gln Phe Pro Asn Ile Leu Leu Glu Gln Gln
                275                 280                 285 atg ata ttt acc cct gag gaa tct gaa gca ggg aat gaa gag gag gaa    914
Met Ile Phe Thr Pro Glu Glu Ser Glu Ala Gly Asn Glu Glu Glu Glu
            290                 295                 300 aaa gag gaa gag aag aaa gag aaa gag gaa atg gaa atg gaa ata atg    962
Lys Glu Glu Glu Lys Lys Glu Lys Glu Glu Met Glu Met Glu Ile Met
        305                 310                 315 gaa atg gag gag gaa aaa gaa gag aga gag gag gag gag gaa aca       1010
Glu Met Glu Glu Glu Lys Glu Glu Arg Glu Glu Glu Glu Glu Thr
    320                 325                 330 caa aaa gaa aag atg gag gaa gag gaa aaa taagagtaga aagaggagga     1060
Gln Lys Glu Lys Met Glu Glu Glu Glu Lys
335                 340 aaaagatgta tcaccaatat aaaccaaaag tgtaatacaa aaaagacag aaaaagaaag   1120 taaaacactg agttttaaca agaaagaaaa tatgcaaacc accattggaa tgtttttttat 1180 tcccttctct cctatactta ttcaatcaat ttaaatttgt aaaacaaaga aacaaaaaaa  1240
atcgaattc                                                          1249

<210> SEQ ID NO 8
<211> LENGTH: 344
<212> TYPE: PRT
<213> ORGANISM: Homosapiens

<400> SEQUENCE: 8

Met Glu Ala Ala Arg Pro Phe Ala Arg Glu Trp Arg Ala Gln Ser Leu
1               5                   10                  15

Pro Leu Ala Val Gly Gly Val Leu Lys Leu Arg Leu Cys Glu Leu Trp
                20                  25                  30

Leu Leu Leu Leu Gly Ser Ser Leu Asn Ala Arg Phe Leu Pro Asp Glu
            35                  40                  45

Glu Asp Val Asp Phe Ile Asn Glu Tyr Val Asn Leu His Asn Glu Leu
        50                  55                  60

Arg Gly Asp Val Ile Pro Arg Gly Ser Asn Leu Arg Phe Met Thr Trp
```

```
                65                  70                  75                  80
Asp Val Ala Leu Ser Arg Thr Ala Arg Ala Trp Gly Lys Lys Cys Leu
                    85                  90                  95

Phe Thr His Asn Ile Tyr Leu Gln Asp Val Gln Met Val His Pro Lys
                100                 105                 110

Phe Tyr Gly Ile Gly Glu Asn Met Trp Val Gly Pro Glu Asn Glu Phe
                115                 120                 125

Thr Ala Ser Ile Ala Ile Arg Ser Trp His Ala Glu Lys Lys Met Tyr
                130                 135                 140

Asn Phe Glu Asn Gly Ser Cys Ser Gly Asp Cys Ser Asn Tyr Ile Gln
145                 150                 155                 160

Leu Val Trp Asp His Ser Tyr Lys Val Gly Cys Ala Val Thr Pro Cys
                165                 170                 175

Ser Lys Ile Gly His Ile Ile His Ala Ala Ile Phe Ile Cys Asn Tyr
                180                 185                 190

Ala Pro Gly Gly Thr Leu Thr Arg Arg Pro Tyr Glu Pro Gly Ile Phe
                195                 200                 205

Cys Thr Arg Cys Gly Arg Arg Asp Lys Cys Thr Asp Phe Leu Cys Ser
    210                 215                 220

Asn Ala Asp Arg Asp Gln Ala Thr Tyr Tyr Arg Phe Trp Tyr Pro Lys
225                 230                 235                 240

Trp Glu Met Pro Arg Pro Val Val Cys Asp Pro Leu Cys Thr Phe Ile
                245                 250                 255

Leu Leu Leu Arg Ile Leu Cys Phe Ile Leu Cys Val Ile Thr Val Leu
                260                 265                 270

Ile Val Gln Ser Gln Phe Pro Asn Ile Leu Leu Glu Gln Gln Met Ile
                275                 280                 285

Phe Thr Pro Glu Glu Ser Glu Ala Gly Asn Glu Glu Glu Lys Glu
                290                 295                 300

Glu Glu Lys Lys Glu Lys Glu Met Glu Met Ile Met Glu Met
305                 310                 315                 320

Glu Glu Glu Lys Glu Glu Arg Glu Glu Glu Glu Glu Thr Gln Lys
                325                 330                 335

Glu Lys Met Glu Glu Glu Glu Lys
                340

<210> SEQ ID NO 9
<211> LENGTH: 1043
<212> TYPE: DNA
<213> ORGANISM: Homosapiens
<220> FEATURE:
<221> NAME/KEY: CDS
<222> LOCATION: (28)..(531)

<400> SEQUENCE: 9
cactggcctg tcagcggccg gtggacc atg gag gcc gca agg ccc ttc gcc cgg    54
                               Met Glu Ala Ala Arg Pro Phe Ala Arg
                                 1               5 gag tgg agg gcc cag tcc cta ccc ctg gca gta ggg ggc gtt ttg aag      102
Glu Trp Arg Ala Gln Ser Leu Pro Leu Ala Val Gly Gly Val Leu Lys
 10                  15                  20                  25 ctg cgg ctc tgt gag ctg tgg cta ctg ctg ggt tct agt ttg aac          150
Leu Arg Leu Cys Glu Leu Trp Leu Leu Leu Gly Ser Ser Leu Asn
                 30                  35                  40 gcc aga ttt ttg cca gac gag gag gac gta gac ttt atc aac gag tac      198
Ala Arg Phe Leu Pro Asp Glu Glu Asp Val Asp Phe Ile Asn Glu Tyr
             45                  50                  55
```

```
gtg aac ctc cac aat gag ctg cgg ggc gac gtc att ccc cga ggg tct     246
Val Asn Leu His Asn Glu Leu Arg Gly Asp Val Ile Pro Arg Gly Ser
         60                  65                  70 aac ttg cgc ttc atg act tgg gat gta gct tta tca cgg act gct aga     294
Asn Leu Arg Phe Met Thr Trp Asp Val Ala Leu Ser Arg Thr Ala Arg
     75                  80                  85 gca tgg gga aaa aaa tgt ttg ttt acg cat aat att tat tta caa gat     342
Ala Trp Gly Lys Lys Cys Leu Phe Thr His Asn Ile Tyr Leu Gln Asp
 90                  95                 100                 105 gta caa atg gtc cat cct aaa ttt tat ggt att ggt gaa aat atg tgg     390
Val Gln Met Val His Pro Lys Phe Tyr Gly Ile Gly Glu Asn Met Trp
                110                 115                 120 gtc ggc cct gaa aat gaa ttt act gca agt att gct atc aga agt tgg     438
Val Gly Pro Glu Asn Glu Phe Thr Ala Ser Ile Ala Ile Arg Ser Trp
            125                 130                 135 cat gca gag aag aaa atg tac aat ttt gaa aat ggc agt tgc tct gga     486
His Ala Glu Lys Lys Met Tyr Asn Phe Glu Asn Gly Ser Cys Ser Gly
        140                 145                 150 gac tgt tct aat tat att cag agg aac act gac gag aag acc tta         531
Asp Cys Ser Asn Tyr Ile Gln Arg Asn Thr Asp Glu Lys Thr Leu
    155                 160                 165 tgaaccagga atattttgta ctcgatgtgg cagacgtgac aaatgcacag attttctatg   591
cagtaatgca gatcgtgacc aagccacata ttaccgattt tggtatccaa aatgggaaat   651
gccccggcca gttgtgtgtg atccactgtg cacattcatt ttattattga gaatattatg   711
ttttatcctg tgtgtcataa ctgttttgat agtacagtct cagtttccaa atatcttgtt   771
ggaacaacaa atgatattta cccctgagga atctgaagca gggaatgaag aggaggaaaa   831
agaggaagag aagaaagaga aggggaaat ggaaatggaa ataatggaaa tggaggagga   891
aaaagaagag agagaggaag aggaggagga aacacaaaaa gaaagatgg aggaagagga   951 aaataagag tagaaagagg aggaaaaaga tgtatcacca atataaacca aaagtgtaat   1011
gcaaaaaaaa aaaaaaaaaa aaaaaaaaaa aa                                 1043
```

<210> SEQ ID NO 10
<211> LENGTH: 168
<212> TYPE: PRT
<213> ORGANISM: Homosapiens

<400> SEQUENCE: 10

```
Met Glu Ala Ala Arg Pro Phe Ala Arg Glu Trp Arg Ala Gln Ser Leu
 1               5                  10                  15

Pro Leu Ala Val Gly Gly Val Leu Lys Leu Arg Leu Cys Glu Leu Trp
                20                  25                  30

Leu Leu Leu Leu Gly Ser Ser Leu Asn Ala Arg Phe Leu Pro Asp Glu
            35                  40                  45

Glu Asp Val Asp Phe Ile Asn Glu Tyr Val Asn Leu His Asn Glu Leu
        50                  55                  60

Arg Gly Asp Val Ile Pro Arg Gly Ser Asn Leu Arg Phe Met Thr Trp
 65                  70                  75                  80

Asp Val Ala Leu Ser Arg Thr Ala Arg Ala Trp Gly Lys Lys Cys Leu
                85                  90                  95

Phe Thr His Asn Ile Tyr Leu Gln Asp Val Gln Met Val His Pro Lys
            100                 105                 110

Phe Tyr Gly Ile Gly Glu Asn Met Trp Val Gly Pro Glu Asn Glu Phe
        115                 120                 125
```

```
Thr Ala Ser Ile Ala Ile Arg Ser Trp His Ala Glu Lys Lys Met Tyr
    130                 135                 140

Asn Phe Glu Asn Gly Ser Cys Ser Gly Asp Cys Ser Asn Tyr Ile Gln
145                 150                 155                 160

Arg Asn Thr Asp Glu Lys Thr Leu
                165

<210> SEQ ID NO 11
<211> LENGTH: 8
<212> TYPE: PRT
<213> ORGANISM: Artificial
<220> FEATURE:
<223> OTHER INFORMATION: Flag peptide

<400> SEQUENCE: 11

Asp Tyr Lys Asp Asp Asp Asp Lys
1               5
```